(12) United States Patent
Scilimati et al.

(10) Patent No.: US 8,017,613 B2
(45) Date of Patent: Sep. 13, 2011

(54) BETA-3 RECEPTOR LIGANDS AND THEIR USE IN THERAPY

(75) Inventors: Antonio Scilimati, Bari (IT); Maria Grazia Perrone, Bari (IT); Ernesto Santandrea, Bari (IT)

(73) Assignee: Universita' Degli Studi Di Bari, Bari (IT)

( * ) Notice: Subject to any disclaimer, the term of this patent is extended or adjusted under 35 U.S.C. 154(b) by 0 days.

(21) Appl. No.: 12/376,324

(22) PCT Filed: Aug. 3, 2007

(86) PCT No.: PCT/IB2007/002230
§ 371 (c)(1),
(2), (4) Date: Feb. 4, 2009

(87) PCT Pub. No.: WO2008/015558
PCT Pub. Date: Feb. 7, 2008

(65) Prior Publication Data
US 2010/0075977 A1    Mar. 25, 2010

(30) Foreign Application Priority Data
Aug. 4, 2006 (IT) .............................. MI2006A1581

(51) Int. Cl.
*A01N 43/00* (2006.01)
*A61K 31/33* (2006.01)
(52) U.S. Cl. ................... 514/252.12; 514/532; 514/358; 544/358; 548/574; 560/42
(58) Field of Classification Search .................. 435/108; 514/486, 543, 532; 544/358; 548/574; 560/42
See application file for complete search history.

(56) References Cited

FOREIGN PATENT DOCUMENTS

| EP | 1 072 583 | 1/2001 |
|----|-----------|--------|
| WO | 93/10074 | 5/1993 |
| WO | 2005/046666 | 5/2005 |

OTHER PUBLICATIONS

Vippagunta et al., Advanced Drug Delivery Reviews, 2001, vol. 48, p. 18, section 3.4.*
Patani et al, Bioisosterism: Rational approach in drug design, Chem. Rev., 1996, 3147-3176.*
International Search Report for PCT/IB2007/002230, mailed May 20, 2008.
Written Opinion of the International Searching Authority for PCT/IB2007/002230, mailed May 20, 2008.
Tanaka et al., ".Beta. 3-Adrenoceptor Agonists for the Treatment of Frequent Urination and Urinary Incontinence: 2-[4-(2-{[1S, 2R)-2-Hydroxy-2-(4-Hydroxyphenyl)-1-Methylethyl]Amino}ethyl)Phenoxy]-2-Methylpropionic Acid", Bioorganic & Medicinal Chemistry, vol. 9, No. 12, 2001, pp. 3265-3271, XP002470671.
Perrone et al, "Stereospecific Synthesis and Bio-Activity of Novel $\beta_3$-adrenoceptor Agonists and Inverse Agonists", Bioorganic & Medicinal Chemistry, 16 (2008) 2473-2488.

* cited by examiner

*Primary Examiner* — Brandon Fetterolf
*Assistant Examiner* — Jean Cornet
(74) *Attorney, Agent, or Firm* — Nixon & Vanderhye P.C.

(57) ABSTRACT

The present invention relates to new compounds, ligands of the beta-3 adrenergic receptor, their preparation and their use in therapy or as research tools for said receptor; the invention also relates to a process for the preparation of the compounds of the invention and the use of inverse agonists of the beta-3 adrenergic receptor as medicaments.

1 Claim, 1 Drawing Sheet

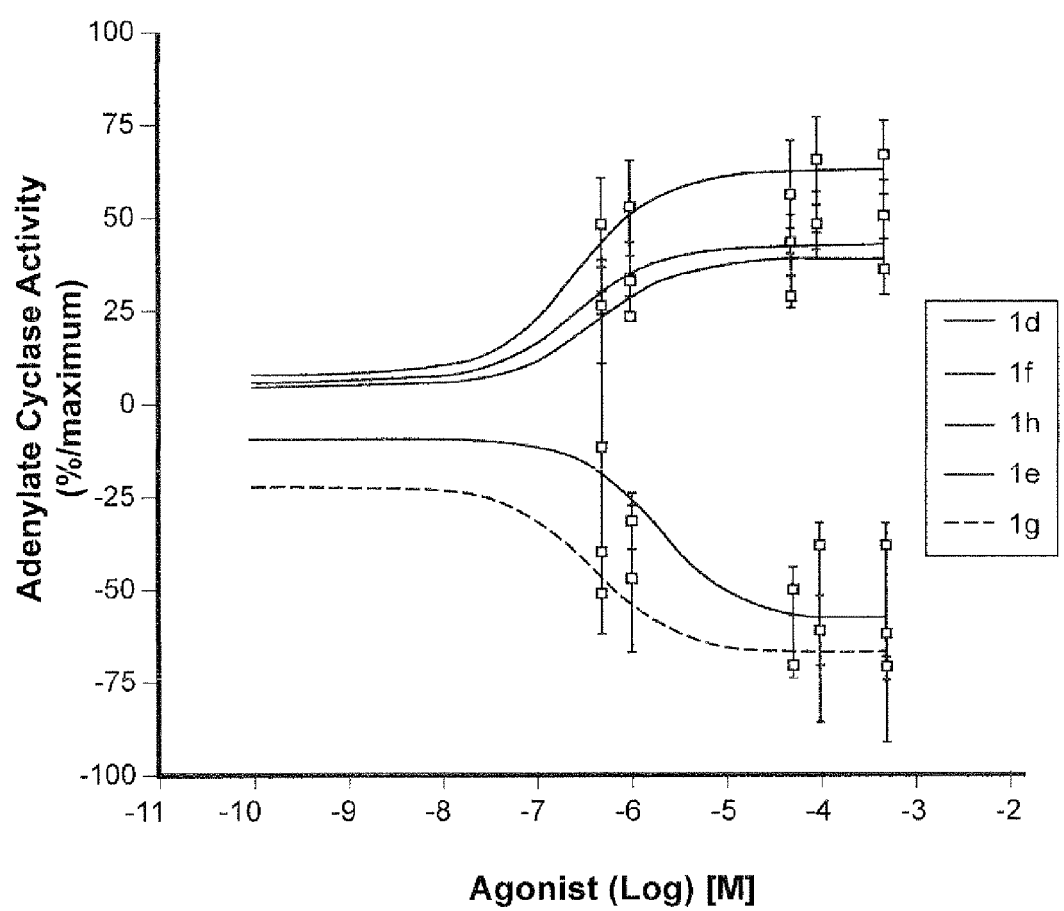

BETA-3 RECEPTOR LIGANDS AND THEIR USE IN THERAPY

This application is the U.S. national phase of International Application No. PCT/IB2007/002230, filed 3 Aug. 2007, which designated the U.S. and claims priority to Italian Application no. MI2006A001581, filed 4 Aug. 2006, the entire contents of which are hereby incorporated by reference.

FIELD OF THE INVENTION

The present invention relates to new compounds which are ligands of the beta-3 adrenergic receptor, their preparation and their use, in therapy or as a research tool for said receptor.

THE TECHNICAL BACKGROUND

The beta adrenergic receptors were classified as beta-1 and beta-2 by 1967. At the beginning of the '80s a new adrenergic receptor—subsequently called beta-3 adrenergic receptor—was discovered to be present in several species, including humans (Proc. Nutr. Soc. 1989, 48:215-223).

The beta-3 adrenergic receptor is expressed in various tissues among which are adipose tissue, heart, uterus, bladder and bowel, where it modulates different functions.

Agonist and antagonist compounds of the beta-3 adrenergic receptor have been synthesized and it has been observed that activation of the receptor by agonist compounds induces thermogenesis and increases sensitivity to insulin; in various animal models such effects cause a reduction of body weight and relieve the symptoms of diabetes.

It has been noticed that an increase in beta-3 adrenergic receptor function in visceral fat deposits can favor an increase in lipolysis and the consequent flux of portal non-esterified fatty-acids, thus causing harmful effects on liver metabolism. In fact, the non-esterified fatty acids stimulate secretion of VLDL ("very low density lipoproteins") and gluconeogenesis and interfere with liver clearance of insulin causing dyslipoproteinemia, glucose intolerance and hyperinsulinemia, with effects on arterial blood pressure.

As stated, agonist and antagonist compounds have been reported, but until now no inverse agonists of the beta-3 adrenergic receptor have been described.

SUMMARY OF THE INVENTION

An object of the present invention is to provide new ligands of the beta-3 adrenergic receptor.

Another object of the present invention is to provide new compounds that are active as agonists of the beta-3 adrenergic receptor.

Another object of the present invention is to provide new compounds that are active as inverse agonists of the beta-3 adrenergic receptor.

Another object of the present invention is to provide new compounds that are active as antagonists of the beta-3 adrenergic receptor.

DESCRIPTION OF THE INVENTION

According to the first aspect, a subject-matter of the invention is a compound of formula (I)

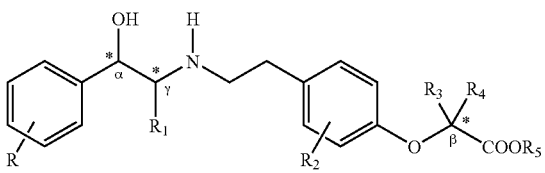

wherein:
R represents a hydrogen atom, a hydroxyl group, an alkoxyl group, an alkyl group, a carbaldoxime group or a halogen atom;
$R_1$ represents a hydrogen atom or a methyl group;
$R_2$ represents a hydrogen atom, a hydroxyl group, an alkoxyl group, an alkyl group or a halogen atom;
$R_3, R_4$ each independently represents an alkyl group or $R_3$ represents an atom of hydrogen and $R_4$ is an alkyl group;
$R_5$ represents a hydrogen atom or an alkyl group; .
and its salts and solvates.

According to the present invention, the term "alkoxyl" designates a lower alkoxyl group, linear or branched, having 1 to 6 carbon atoms. The preferred alkoxyl is the methoxyl group.

According to the present invention, the term "alkyl" designates a lower alkyl group, linear or branched, having 1 to 6 carbon atoms. The preferred alkyl is the methyl group.

"Halogen atom" according to the present invention is intended as one of the four halogens: bromine, chlorine, fluorine and iodine; chlorine and bromine are preferred. "Solvates" according to the present invention is intended to mean a complex formed by one of the compounds of the invention with a solvent, for instance with one or more molecules of the solvent being used to isolate the compound of the invention. The solvates of the invention include hydrates.

According to a preferred aspect of the present invention, the radical R is in the para or meta position on the phenyl.

According to another preferred aspect of the present invention, the radical R is a hydrogen atom, a hydroxyl group or a halogen atom—preferably chlorine.

According to another preferred aspect of the present invention, the radical $R_1$ is a hydrogen atom or a methyl group.

According to another preferred aspect of the present invention, the radical $R_3$ is a hydrogen atom and the radical $R_4$ is a methyl group.

According to another preferred aspect of the present invention, the radicals $R_3$ and $R_4$ each represents a methyl group.

According to another preferred aspect of the present invention, the radical $R_5$ is a hydrogen atom or a methyl or ethyl group.

According to another aspect, the invention concerns a compound of formula (II)

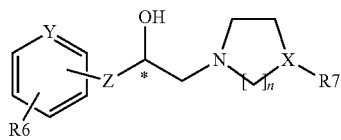

wherein
Y is CH or N;
Z is a direct bond or a —O—CH$_2$— group wherein the oxygen atom is bound to the ring;

n is 0, 1 or 2, provided that when n is 1 or 2, X is N and when n is 0, X is NH, O or S;

$R_6$ is a hydrogen atom, an alkyl group, an optionally substituted aryl group, a optionally substituted heteroaryl group, a halogen atom, —OH, $NH_2$, —O-alkyl, optionally substituted-O-aryl, optionally substituted-O-heteroaryl, —NH—CO—$R_8$—, optionally substituted NH—CO-aryl, optionally substituted-NH—CO-heteroaryl, NH—$SO_2$-alkyl, optionally substituted NH—$SO_2$-aryl, optionally substituted NH—$SO_2$-heteroaryl, NH—$SO_2$—$R_8$, a nitro group; or when Y is CH, $R_6$ is an aromatic group or heteroaromatic fused with the benzene ring to form a naphthalene or carbazole group;

$R_7$ is $R_8SO_2$—, $R_8CO$—, —CO-aryl optionally substituted, optionally substituted-CO-heteroaryl, optionally substituted $SO_2$-aryl, optionally substituted $SO_2$-heteroaryl;

$R_8$ is an alkyl group;

and its salts and solvates.

When n is 0, the structure comprising the nitrogen atom and X is open.

Preferred compounds of formula (II) include those wherein n is 2.

Preferred compounds of formula (II) include those wherein n is 2 and X is N. The preferred aryl groups include: 1-, 2-naphthyl; 2-, 3- or 4-methoxyphenyl; 2-, 3- or 4-(halogen) phenyl; 2-, 3- or 4-nitrophenyl; 2-, 3- or 4-aminophenyl; 2-, 3- or 4-alkylphenyl; 2-, 3- or 4-carboxyphenyl.

Preferred heteroaryl groups include: pyridin-2-yl; pyridin-3-yl; pyridin-4-yl; indol-2-yl; indol-3-yl; indol-4-yl; indol-5-yl; indol-6-yl; indol-7-yl; 2-thienyl; 3-thienyl; 2-, 3-, 4-, 5-, 6-, 7-benzofuranyl; 2-furyl; 3-furyl; 2-, 4-, 5-; 6-, 7-benzothiazolyl; 2-, 4-, 5-, 6-, 7-benzoimidazolyl; 2-, 3-, 4-, 5-, 6-, 7-, 8-quinolinyl; 1,3-, 4-, 5-, 6-, 7-, 8-isoquinolinyl; 1-, 2-, 3-, 4-carbazolyl.

Preferred compounds of formula (II) are compounds wherein Z is a —O—$CH_2$— group wherein the oxygen atom is bound to the ring and the Y group is a nitrogen atom or CH.

Other preferred compounds of formula (II) are compounds wherein Y is CH and $R_6$ is a hydrogen atom, a hydroxyl, amino, benzyloxy or nitro group.

Other preferred compounds of formula (II) are compounds wherein Y is CH and $R_6$ is an aromatic or heteroaromatic group fused with the benzene ring to form a naphthalene or carbazole group.

Other preferred compounds of formula (II) are the compounds wherein $R_6$ is a sulfonylamino group substituted with an alkyl group, such as, for instance, the methyl group, or substituted with an aryl group, such as the phenyl group or substituted with a heteroaryl group, such as the thienyl group.

Other preferred compounds of formula (II) are the compounds wherein $R_6$ is a hydroxyl group or a halogen.

The salts of the compounds of formula (I) and (II) must be pharmaceutically acceptable when they have to be administered to humans or to animals. Alternatively, when said salts are prepared for purifying the compounds of formula (I) or (II) or as a reaction intermediates or in the use of compounds of formula (I) or (II) as a research tool for the beta-3 adrenergic receptor, it is not necessary that said salts be pharmaceutically acceptable.

Examples of useful salts according to the invention are for instance salts with alkaline metals or alkaline earth metals such as sodium, potassium, magnesium, calcium, salts etc., or salts with amines such as the salts with tromethamine and similar, chlorhydrate, bromhydrate, sulfates, oxalate and the like.

Carbon atoms marked by asteriski are, or can be, chiral carbon atoms.

In particular, the carbon atom carrying the hydroxyl group (here below also "position α") is always chiral and the compounds of formula (I) and (II) can then present in (R) or (S) forms or in a mixture of (R)/(S) forms.

Furthermore, the carbon atom carrying the $R_1$ group (here below also "position γ") is chiral and the compounds of formula (I) when $R_1$ is different from hydrogen, for example $R_1$=methyl, can then present in (R) or (S) form or in a mixture of (R)/(S) forms.

The carbon atom carrying the radicals $R_3$ and $R_4$ (here below also "position n") of the compounds of formula (I) is chiral only when the two radicals represent different substituents, i.e. for instance when $R_3$ is a hydrogen atom and $R_4$ is an alkyl group or when they represent two different alkyl groups. In this case, this carbon atom of can also present in the (R) or (S) form or as a mixture of (R)/(S) form.

The racemate, the diastereoisomers, the enantiomers and the compounds of these in any relative proportions are all subject-matter of the present invention.

Preferred compounds of formula (I) according to the invention are the following:

(±)2-[4-[2-(2-phenyl-2-hydroxyethylamino)ethyl]phenoxy]-2-methylpropionic acid (1a);

2-[4-[2-((2R)-2-phenyl-2-hydroxyethylamino)ethyl]phenoxy]-2-methylpropionic acid (1b);

2-[4-[2-((2S)-2-phenyl-2-hydroxyethylamino)ethyl]phenoxy]-2-methylpropionic acid (1c);

(±)-2-[4-[2-(2-phenyl-2-hydroxyethylamino)ethyl]phenoxy]propionic acid (1d);

(2S)-2-[4-[2-((2S)-2-phenyl-2-hydroxyethylamino)ethyl]phenoxy]propionic acid (1e);

(2S)-2-[4-[2-((2R)-2-phenyl-2-hydroxyethylamino)ethyl]phenoxy]propionic acid (1f);

(2R)-2-[4-[2-((2S)-2-phenyl-2-hydroxyethylamino)ethyl]phenoxy]propionic acid (1g);

(2R)-2-[4-[2-((2R)-2-phenyl-2-hydroxyethylamino)ethyl]phenoxy]propionic acid (1h);

2-[4-[2-((2R)-2-(3-chlorophenyl)-2-hydroxyethylamino) ethyl]phenoxy]-2-methylpropionic acid (1i);

(R)-2-[4-[2-((1S,2R)-1-hydroxy-1-phenylpropan-2-ylamino)ethyl]phenoxy]propionic acid (1j);

(R)-2-[4-[2-((1S,2S)-1-hydroxy-1-phenylpropan-2-ylamino)ethyl]phenoxy]propionic acid (1k);

and their salts, their solvates and their esters with alkyl groups.

Other preferred compounds of formula (II) according to the invention are the following:

(S)-1-phenoxy-2-hydroxy-3-[4-(4-methoxybenzenesulfonyl)piperazin-1-yl]propane (2a)

(S)-1-(4-hydroxyphenoxy)-2-hydroxy-3-[4-(4-methoxybenzenesulfonyl)piperazin-1-yl]propane (2b);

(S)-1-(4-benzyloxyphenoxy)-2-hydroxy-3-[4-(4-methoxybenzenesulfonyl)piperazin-1-yl]propane (2c);

(S)-1-(3-nitrophenoxy)-2-hydroxy-3-[4-(4-methoxybenzenesulfonyl) piperazin-1-yl]propane (2d);

(S)-1-(3-aminophenoxy)-2-hydroxy-3-[4-(4-methoxybenzenesulfonyl)piperazin-1-yl]propane (2e);

(S)-2-hydroxy-1-(3-metanesulfonylaminophenoxy)-3-[4-(4-methoxyphenylsulfonyl)piperazin-1-yl]propane (2f);

(S)-1-(3-benzenesulfonylaminophenoxy)-2-hydroxy-3-[4-(4-methoxyphenylsulfonyl)piperazin-1-yl]propane (2g);

(S)-2-hydroxy-3-[4-(4-methoxyphenylsulfonyl)piperazin-1-yl]-1-(3-thiophenesulfonylaminophenoxy)propane (2h);

(S)-2-hydroxy-3-[4-(4-methoxyphenylsulfonyl)piperazin-1-yl]-1-(napht-1-yloxy)propane (2i);

(S)-1-(carbazol-4-yloxy)-2-hydroxy-3-[4-(4-methoxybenzenesulfonyl)piperazin-1-yl]propane (2j);

and their salts, their solvates.

The compounds of formula (I) and (II) possess interesting activity on the beta-3 adrenergic receptor.

The use of compounds of formula (I) and (II) as ligands of the beta-3 adrenergic receptor constitutes another subject-matter of the invention.

More specifically, the compounds of formula (I) wherein the chiral carbon atom that carries the hydroxyl group is in (R) form generally has agonist or partial agonist activity on the beta-3 adrenergic receptor.

The compound of formula (I) (2S)-2-[4-[2-((2R)-2-phenyl-2-hydroxyethylamino)ethyl]phenoxy]propionic acid (1f), for instance, is a particularly active compound as agonist of the beta-3 adrenergic receptor.

Surprisingly, however, it has now been found that (±)2-[4-[2-(2-phenyl-2-hydroxyethylamino)ethyl]phenoxy]-2-methylpropionic acid (1a) behaves as an agonist of the beta-3 adrenergic receptor independently of the configuration of the chiral atom.

This way, according to another of its aspects, the invention relates to the use of a compound selected from:
(±)-2-[4-[2-(2-phenyl-2-hydroxyethylamino)ethyl]phenoxy]-2-methylpropionic acid (1a),
2-[4-[2-((2R)-2-phenyl-2-hydroxyethylamino)ethyl]phenoxy]-2-methylpropionic acid (1b),
2-[4-[2-(2S)-2-phenyl-2-hydroxyethylamino)ethyl]phenoxy]-2-methylpropionic acid (1c),
and their salts, solvates or their alkyl esters derivatives as agonists of the beta-3 adrenergic receptor in the treatment of obesity, diabetes, overactive bladder, ulcero-inflammatory disorders of the gut, heart failure, anxiety, depressive disorders and for the preterm labor.

It has been found, furthermore, that some compounds of formula (I) have activity as inverse agonists of the beta-3 adrenergic receptor and they represent a preferred aspect of the present invention.

Specifically, the compounds of formula (I) wherein the chiral carbon atom that carries the hydroxyl group is in (S) form, such as:
(2S)-2-[4-[2((2S)-2-phenyl-2-hydroxyethylamino)ethyl] phenoxy]propionic acid (1e);
(2R)-2-[4-[2-((2S)-2-phenyl-2-hydroxyethylamino)ethyl] phenoxy]propionic acid (1g);
and their salts, solvates and esters with alkyl groups, present inverse agonist activity of the beta-3 adrenergic receptor and are useful for the preparation of medicaments for the treatment of metabolic syndrome, heart failure and for the prevention of cachexias of diverse origin (for instance, neoplasm type and others).

Alternatively, the compounds of the invention with inverse agonist activity of the beta-3 adrenergic receptor can be used as research tools (also "laboratory tool") for said receptor.

The use of the inverse agonists of the beta-3 adrenergic receptor for the preparation of medicaments for the treatment of metabolic syndrome, of heart failure and of cachexias constitutes a further subject-matter of the invention.

In the experimental section of the present description, the results of the pharmacological tests are also reported.

The compounds of formula (I) can be prepared by a process that comprises N-alkylation of a compound of formula (III)

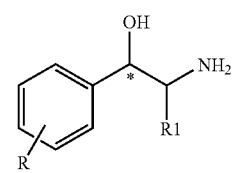

where R and $R_1$ are as previously defined, with a compound of formula (IV)

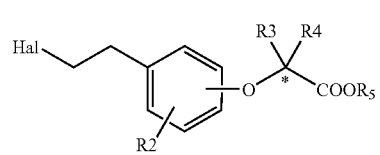

where $R_2$, $R_3$ and $R_4$ are as previously defined, $R_5$ is an alkyl group and Hal represents a halogen atom, advantageously an atom of bromine or chlorine and, optionally, hydrolyzed to give the compound of formula (I) where $R_5$ is a hydrogen atom.

The compounds of formula (II) wherein Z is a group-$CH_2$—O— can be prepared by a process that comprises reacting a compound of formula (V)

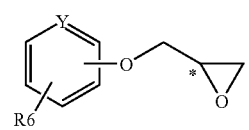

wherein $R_6$ and Y are as defined above, with a compound of formula (VI)

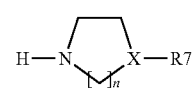

wherein $R_7$ and X and n are as defined above, by heating in an suitable solvent.

The compounds of formula (II) wherein Z is a direct bond can be prepared by a process that comprises reacting a compound of formula (VII)

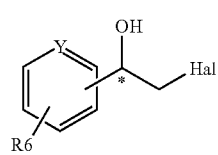

wherein $R_6$ and Y are as defined above and Hal is a halogen atom, with a compound of formula (VI)

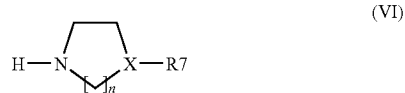

wherein $R_7$ and X and n are as defined above, by heating in an suitable solvent.

The compounds of formula (III), (IV), (V), (VI) and (VII) can be prepared according to methods already known. Some examples of preparation are included in the Experimental Section of the present invention, by way of example.

For their use as medicaments, the compounds of formula (I) and (II) can be formulated as pharmaceutical compositions.

According to another of its aspects, the invention also comprises to pharmaceutical compositions containing a compound of formula (I) and (II) or one of its pharmaceutically acceptable salts or solvates as active principle, optionally in combination with one or more appropriate inert excipients.

The pharmaceutical compositions of the invention are preferably administered in the form of dosage units. In each dosage unit, the active principle of formula (I) and (II) is present in the appropriate amounts for the prescribed daily dosage. Every dosage unit is suitably prepared according to the dose and the type of administration foreseen.

The dosage can vary broadly depending on the age, weight and state of health of the patient, the nature and the severity of the condition and also on the method of administration and is determined by the doctor who prescribes the medicament.

Appropriate unitary forms of administration include oral forms such as tablets, capsules, powders, granules and solutions or oral suspensions, of sub-lingual and buccal forms, subcutaneous, intramuscular or intravenous administration forms, intranasal or intraocular forms, rectal administration forms and can be prepared with the necessary pharmaceutical excipients.

Typical pharmaceutical excipients used for the preparation of pharmaceutical compositions, ratio of content of the excipients to the active principle and methods of preparing the pharmaceutical composition can be chosen appropriately by the skilled in the art. Organic or inorganic substances, solid or liquid substances can be used as pharmaceutical excipients. The pharmaceutical excipients can generally be incorporated in a quantity that varies from 1% by weight to 99% by weight on the basis of the weight of active principle.

Examples of excipients used for the preparation of solid pharmaceutical compositions include, for example, lactose, saccharin, starch, talc, cellulose, dextrin, kaolin, calcium carbonate and similar. For the preparation of liquid compositions for oral administration, a conventional inert diluent such as water or a vegetable oil can be used. The liquid composition can also contain besides the inert diluent, auxiliary agents, such as wetting agents, agents of suspension, sweeteners, fragrances, dyes and preservatives. The liquid composition can be enclosed in capsules of an absorbable material such as gelatin. Examples of solvents or means of suspension for the preparation of compositions for parenteral administration (e.g. injection, suppository) comprise water, propylene glycol, polyethylene glycol, benzyl alcohol, the ethyl oleate of lecithin and similar. Examples of material bases used for suppositories include, for instance, cocoa butter.

The following non-limiting examples, illustrate the invention.

EXPERIMENTAL SECTION

Compounds of Formula (I)

Example 1

Ethyl esters of the (±)-2-[4-[2-(2-phenyl-2-hydroxyethylamino)ethyl]phenoxy]-2-methylpropionic acid
(a)

A compound of 2-[4-(2-bromoethyl)phenoxy]-2-methylpropionic ethyl ester and of racemic 2-amino-1-phenylethanol, in approximately equimolar ratio, in anhydrous N,N-dimethylformamide is maintained in agitation at 70° C. for 70 hours under a nitrogen atmosphere. Ethyl acetate is added to the reaction mixture, the mixture is washed with a saturated NaCl solution and dried on $Na_2SO_4$. The solvent is removed under vacuum and the product isolated by column chromatography (silica gel, petroleum ether/ethyl acetate=8:2. Yield=80%. FT-IR (liquid film): 3600-3100, 3060, 3032, 2989, 2935, 2854, 1733, 1611, 1509, 1454, 1383, 1266, 1235, 1179, 1144, 1026, 914, 850, 736, 702 $cm^{-1}$. $^1$NMRs (300 MHz, $CDCl_3$, d)): 1.24 (t, J=7.1 Hz, 3H, $OCH_2CH_3$), 1.56 (s, 6H, $C(CH_3)_2$), 2.70-2.96 (m, 6H, $CH_2CHOH$, $CH_2NH$, $CH_2CH_2NHNH$), 3.90-4.10 (bs, 2H, OH and NH: exchanged with $D_2O$), 4.22 (q, J=7.1 Hz, 2H, $OCH_2$ $CH_3$), 4.75 (dd, J=9.2 and 3.4 Hz, 1H, CHOH), 6.75-6.78 (m, 2H, aromatic protons), 7.00-7.03 (m, 2H, aromatic protons), 7.23-7.33 (m, 5H, aromatic protons). $^{13}$C NMRs (75 MHz $CDCl_3$, δ): 14.31, 25.58, 35.54, 50.88, 57.12, 61.62, 71.82, 79.31, 119.67, 126.03, 127.73, 128.60, 129.54, 133.46, 142.84, 154.03, 174.59. GC-MS (70 eV) m/z (int. rel.): 353 [(M−18)+, 4], 298 (11), 264 (100), 238 (9), 235 (7), 150 (25), 132 (68), 121 (44), 107 (24), 91 (11), 77 (12), 43 (8). Anal. ($C_{22}H_{29}NO_4$): C, H, N.

Example 2

Ethyl esters of (±)-2-[4-[2-(2-phenyl-2-hydroxyethylamino)ethyl]phenoxy]propionic acid (d)

A compound of ethyl ester of the 2-[4-(2-bromoethyl)phenoxy]propionic acid and of racemic. 2-amino-1-phenylethanol, in approximately equimolar ratio, in anhydrous N,N-dimethylformamide is maintained in agitation at 70° C. for 70 hours under nitrogen atmosphere. Then the compound is diluted with ethyl acetate, washed with saturated NaCl solution and dried on $Na_2SO_4$. The solvent is removed under vacuum and the product isolated by chromatography (silica gel, dichloromethane/ethanol=40:1. Yield=49%. FT-IR (liquid film): 3600-3100, 3058, 3022, 2986, 2935, 2855, 1750, 1669, 1612, 1581, 1511, 1449, 1375, 1292, 1239, 1135, 1050, 1014, 826, 733, 702 $cm^{-1}$. $^1$NMRs (300 MHz $CDCl_3$, δ): 1.23 (t, J=7.1 Hz, 3H, $OCH_2$ $CH_3$), 1.58 (d, J=6.8 Hz, 3H, $CHCH_3$), 2.66-3.00 (m, 6H, $CH_2CHOH$, $CH_2NH$, $CH_2CH_2NH$), 4.20 (q, J=7.1 Hz, 2H, $OCH_2$ $CH_3$), 4.70 (q, J=6.8 Hz, 2H, $CHCH_3$), 4.86 (dd, J=9.3 and 3.3 Hz, 1H, CHOH), 5.10-5.30 (bs, 2H, OH and NH: exchanged with $D_2O$), 6.74-6.82 (m, 2H, aromatic protons), 6.97-7.12 (m, 2H, aromatic protons), 7.24-7.35 (m, 5H, aromatic protons). $^{13}$C NMRs (75 MHz $CDCl_3$, δ): 14.35, 34.29, 50.50, 56.52, 61.47, 66.05, 72.90, 115.51, 126.03, 127.86, 128.66, 129.94, 131.84, 142.28, 156.52, 172.47. GC-MS (70 eV) m/z (int. rel.): 339 [(M−18)+, 1], 284 (4), 250 (100), 221 (24), 207 (7), 176 (10), 150 (14), 147 (14), 132 (69), 121 (19), 107 (18), 105 (14), 104 (10), 103 (11), 91 (10), 77 (14), 43 (9). Anal. ($C_{21}H_{27}NO_4$): C, H, N.

Examples (3-8)

Operating as described in the Examples 1 or 2 but using the appropriate compounds of formula (III) and (IV) the followings compounds are obtained:

Ethyl esters of (−)-2-{4-[2-(R)-2-phenyl-2-hydroxyethylamino)ethyl]phenoxy}-2-methylpropionic acid (b)

Example 3

Yield=64%. [α]D=−32.1 (c=1.0, CH $Cl_3$). The analytical data are identical to those of (2a).

Ethyl esters of (+)-2-{4-[2-((S)-2-phenyl-2-hydroxyethylamino)ethyl]phenoxy}-2-methylpropionic acid (c)

Example 4

Yield=61%. [α]D=+32.0 (c=1.0, CH $Cl_3$). The analytical data are identical to those of (2a)

Methyl ester of (2S)-2-{4-[2-((2S)-2-phenyl-2-hydroxyethylamino)ethyl]phenoxy propionic acid (d)

Example 5

Yield=31%. [α]D=+11.8 (c=0.95, CH $Cl_3$). FT-IR (liquid film): 3600-3200, 3029, 2987, 2937, 2885, 1752, 1612, 1585, 1512, 1451, 1426, 1377, 1348, 1299, 1250, 1207, 1181, 1137, 1100, 1071, 1047, 825, 758, 700 $cm^{-1}$. $^1$NMRs (400 MHz $CDCl_3$, δ): 1.57 (d, J=6.7 Hz, 3H, $CHCH_3$), 2.69-2.93 (m, 6H, $CH_2CHOH$, $CH_2NH$, $CH_2CH_2NH$), 3.45-3.64 (bs, 2H, OH and NH: exchanged with $D_2O$), 3.71 (s, 3H, $OCH_3$), 4.70 (q, J=6.7 Hz, 2H, $CHCH_3$), 4.74 (dd, J=9.3 and 3.2 Hz, 1H, CHOH), 6.75-6.77 (m, 2H, aromatic protons), 7.03-7.05 (m, 2H, aromatic protons), 7.21-7.24 (m, 1H, aromatic proton), 7.27-7.32 (m, 4H, aromatic protons). $^{13}$C NMRs (100 MHz $CDCl_3$, δ) 18.83, 35.05, 50.79, 52.56, 56.91, 71.53, 72.81, 115.36, 126.03, 127.80, 128.63, 129.99, 132.50, 142.51, 154.31, 173.01. GC-MS (70 eV) m/z (int. rel.): 325 [(M−18)+, 9], 325 (41), 324 (25), 238 (31), 206 (24), 193 (40), 147 (30), 134 (30), 132 (100), 130 (21), 120 (20), 107 (44), 106 (21), 105 (50), 104 (45), 103 (30), 91 (69), 90 (20), 78 (20), 77 (38), 70 (25), 51 (19). MS-ESI m/z (%): 344 [M+11]$^+$(100%). Anal. ($C_{20}H_{25}NO_4$): C, H, N.

Methyl ester of (2S)-2-{4-[2-((2R)-2-phenyl-2-hydroxyethylamino)ethyl]phenoxy}propionic acid (f)

Example 6

Yield=47%. [α]D=−58.5 (c=1.05, CH $Cl_3$). The analytical data are identical to those of (e).

Ethyl esters of the acid (2R)-2-{4-[2-((2S)-2-phenyl-2-hydroxyethylamino)ethyl]phenoxy}propionic (g)

Example 7

Yield=66%. [α]D=+55.6 (c=1.01, CH $Cl_3$). The analytical data are identical to those of (d).

Ethyl esters of (2R)-2-{4-[2-((2R)-2-phenyl-2-hydroxyethylamino)ethyl]phenoxy}propionic acid (h)

Example 8

Yield=54%. [α]D=−6.9 (c=0.96, CH $Cl_3$). The analytical data are identical to those of (d).

Example 9

Ethyl esters of 2-[4-[2-((R)-2-(3-chlorophenyl)-2-hydroxyethylamino)ethyl]phenoxy]-2-methylpropionic acid (I)

KI (158 mg, 0.95 mM) is added to a compound of ethyl 2-[4-(2-bromoethyl)phenoxy]-2-methylpropane (500 g, 1.59 mM) in anhydrous DMF (16 ml). The suspension is maintained in agitation for 30 minutes at a temperature of 110° C. and subsequently $NaN_3$ (382 mg, 5.87 mM) is added. The reaction is monitored by GC analysis and after 14 hours the reaction is stopped by adding ethyl acetate and washing the organic phase with water. The product is isolated by column chromatography (silica gel; mobile phase: ethyl acetate/petroleum ether=3:7) of the crude reaction product. 357 mg of ethyl 2-[4-(2-azidoethyl)phenoxy]-2-methylpropane is produced as yellow oil (yield of 97%). FT-IR (neat): 3439, 3328, 2981, 2921, 2871, 2099, 1733, 1611, 1510, 1464, 1381, 1366, 1347, 1281, 1237, 1178, 1140, 1024, 972, 909, 850, 836, 768 $cm^{-1}$; $^1$H NMRs (400 MHz $CDCl_3$, δ): 7.07-7.05 (d, 2H, J=8.6 Hz, aromatic protons); 6.79-636 (d, 2H, J=8.6 Hz; aromatic protons); 4.24-4.18 (q, 2H, J=7.1 Hz, $CH_2$ $CH_3$); 3.45-3.41 (t, 2H, J=7.2 Hz, $CH_2C_6H_4$); 2.82-2.78 (t, 2H, J=7.2 Hz, $CH_2N_3$); 1.56 (s, 6H, $C(CH_3)_2$). 1.24-1.21 (t, 3H, J=7.1 Hz, $CH_3CH_2$).

Pd/C at 10% (16 mg) is added to a solution of ethyl 2-[4-(2-azidoethyl)phenoxy]-2-methylpropane (784 mg, 2.89 mM) in methanol (42 ml) and the suspension is maintained in agitation for the whole night at a pressure of 5 atmospheres of $H_2$ at room temperature until the substrate disappears [TLC (silica gel; mobile phase: ethyl acetate/petroleum ether=2:8)]. The mixture is filtered to remove the catalyst and the solvent is removed at reduced pressure. 539 mg of ethyl 2-[4-(2-aminoethyl)phenoxy]-2-methylpropane is obtained as a colorless oil (74% of yield). FT-IR (neat): 3366, 2985, 2922, 2851, 1732, 1610, 1579, 1508, 1467, 1382, 1362, 1283, 1235, 1177, 1140, 1023, 971, 908, 836, 768 $cm^{-1}$; $^1$H NMRs (400 MHz CD $Cl_3$, δ): 7.06-7.04 (d, 2H, J=8.6 Hz, aromatic protons); 6.78-6.76 (d, 2H, J=8.6 Hz, aromatic protons); 5.70-5.55 (m, 2H, $NH_2$); 4.25-4.19 (q, 2H, J=7.1 Hz, $CH_2CH_3$); 2.96-2.92 (t, 2H, J=7.0 Hz, $CH_2C_6H_4$); 2.76-2.69 (m, 2H, $CH_2NH_2$); 1.56 (s, 6H, $C(CH_3)_2$); 1.26-1.22 (t, 3H, J=7.1 Hz, $CH_3CH_2$). $^{13}$C NMRs (100 MHz $CDCl_3$, δ): 174.33, 153.84, 132.84, 129.42, 119.34, 79.04, 61.37, 43.07, 38.13, 25.32, 14.06. MS-ESI m/z (%): 252 [M+H]$^+$(100). MS-MS (252): 235 (100), 121 (13).

A compound of ethyl 2-[4-(2-aminoethyl)phenoxy]-2-methylpropane (539 mg, 2.15 mM) and (R)-styreneoxide (361 g, 2.33 mM) in $CH_3OH$ anhydrous (19 ml) is refluxed for 4 days. The reaction is monitored by GC analysis. The solvent is removed at reduced pressure and from the residue the product is isolated by column chromatography (silica gel; mobile phase: dichloromethane/ethanol=40:1 and subsequently 20:1). 229 mg of ethyl ester of 2-[4-[2-((R)-2-(3-chlorophenyl)-2-hydroxyethylamino)ethyl]phenoxy]-2-methylpropionic acid is obtained as an orange oil (26% of yield). [α]D=−16.9 (c 0.811, CH $Cl_3$). $^1$H NMRs (400 MHz $CDCl_3$, δ): 7.35 (s, 1H, NH); 7.22-7.18 (m, 4H, aromatic protons); 7.03-7.01

(d, 2H, J=8.6 Hz, aromatic protons); 6.76-6.74 (d, 2H, J=8.6 Hz, aromatic protons); 4.76-4.73 (dd, 1H, J=3.3 and 9.3 Hz, CHOH); 4.38 (bs, OH); 4.24-4.18 (q, 2H, J=7.1 Hz, CH$_2$CH$_3$); 2.94-2.70 (m, 6H, CH$_2$CH$_2$ and CHOHCH$_2$); 1.55 (s, 6H, C(CH$_3$)$_2$); 1.25-1.21 (t, 3H, J=7.1 Hz, CH$_3$CH$_2$). $^{13}$C NMRs (100 MHz CDCl$_3$, δ): 174.27, 153.91, 144.43, 134.30, 132.53, 129.67, 129.95, 127.62, 125.94, 123.92, 119.39, 79.05, 70.42, 61.38, 56.37, 50.38, 34.62, 25.31, 14.06. MS-ESI m/z (%): 406 [M+H]$^+$(100). MS-MS (406): 388 (100), 274 (7), 235 (52), 121 (44).

Example 10

Ethyl esters of (R)-2-[4-[2-((1S,2R)-1-hydroxy-1-phenylpropan-2-yl-amino)ethyl]phenoxy]propionic acid (j)

A compound of (1S,2R)-(+)-Norephedrine (194 mg, 1.0 mM) and ethyl (R)-2-[4-(2-bromoethyl)phenoxy]propane (620 mg, 2.1 mM) in anhydrous DMF (2.2 nil) is maintained in agitation at 70° C. for 2 hours. The reaction mixture is then cooled, treated with ethyl acetate and washed with a saturated aqueous solution of NaHCO$_3$ and a saturated aqueous solution of NaCl. The organic phase is dried with anhydrous Na$_2$SO$_4$, filtered and the solvent removed at reduced pressure. The product is isolated by column chromatography (silica gel; mobile phase: CH$_2$Cl$_2$/EtOH=40:1). 225 mg (43% of yield) is obtained as a yellow solid. Pf 66.7-69.4° C.s. [α]D=+19.6 (c 0.84, CH Cl$_3$). FT-IR (neat): 3337, 2937, 2849, 1751, 1612, 1584, 1507, 1450, 1377, 1240, 1200, 1135, 1050, 1015, 824, 740, 703 cm$^{-1}$; $^1$H NMRs (300 MHz, CDCl$_3$, δ): 7.40-7.20 (m, 5H, aromatic protons); 7.11-7.08 (d, 2H, aromatic protons); 6.81-6.78 (d, 2H, aromatic protons); 4.92-4.91 (d, 1H, J=3.6 Hz, CHOH); 4.74-4.67 (q, 1H, J=6.7 Hz, CH$_3$CHCOO); 4.24-4.17 (q, 2H, J=7.2 Hz, CH$_2$CH$_3$); 3.77-3.66 (bs, 2H, OH and NH: exchanged with D$_2$O); 3.04-2.80 (m, 5H, CH$_3$CHNH and CH$_2$CH$_2$); 1.61-1.60 (d, 3H, J=6.7 Hz, OCHCH$_3$); 1.26-1.22 (t, 3H, J=7.2 Hz, CH$_3$CH$_2$); 0.85 (d, 3H, J=6.6 Hz, CH$_3$CHNH). $^{13}$C NMRs (75 MHz CDCl$_3$, δ): 172.52, 156.48, 141.14, 132.13, 129.96, 128.38, 127.40, 126.19, 115.47, 72.91, 61.51, 59.10, 48.44, 34.84, 18.80, 14.37, 13.34. MS-ESI m/z (%): 372 [M+H]$^+$ (100); 394 [M+Na]$^+$(39). MS-MS (372): 354 (100), 221 (47), 147 (17), 121 (7). Analysis Calc. for C$_{22}$H$_{29}$NO$_4$: C, 71.67; H, 7.87; N, 3.77. Found: C, 71.61; H, 7.59; N, 3.66.

Example 11

Ethyl esters of (R)-2-[4-[2-((4S,5S)-4-methyl-5-phenylozazolidin-2-one)ethyl]phenoxy]propionic acid (k)

A compound ethyl(R)-2-[4-(2-bromoethyl)phenoxy]propane (450 mg, 1.5 mM) and (1R,2S)-Norephedrine in DMF (5 ml) it is maintained in agitation in nitrogen atmosphere at a temperature of 70° C. for 72 hours. Then the reaction mixture is diluted with ethyl acetate, washed with a saturated solution of NaCl and dried with anhydrous Na$_2$SO$_4$. The solvent is removed at reduced pressure and the product is isolated from the residue by column chromatography (silica gel; mobile phase: dichloromethane/ethanol=40:1). 145 mg of ethyl (R)-2-[4-[2-((1R,2S)-1-hydroxy-1-phenylpropan-2-yl-amino)ethyl]benzyl]propane is obtained as clear yellow oil (52% of yield). [α]D=−0.6 (c 1.1, CH Cl$_3$). FT-IR (neat): 3262, 3055, 2986, 2930, 1748, 1613, 1559, 1511, 1451, 1270, 1241, 1196, 1136, 1098, 1051, 1016, 743, 703 cm$^{-1}$. $^1$NMRs (500 MHz, CDCl$_3$, δ): 7.32-7.22 (m, 5H, aromatic protons); 7.11-7.09 (2H, aromatic protons); 6.80-6.78 (2H, aromatic protons); 5.15-5.14 (d, 1H, J=4.0 Hz, CHOH); 4.76 (bs, 2H, OH and NH: exchanged with D$_2$O); 4.71-4.67 (q, 1H, J=6.7 Hz, CH$_3$CHCO); 4.22-4.18 (q, 1H, J=7.2 Hz, CH$_2$CH$_3$); 3.71-3.67 (q, 1H, J=7.0 Hz, CH$_3$CHNH); 3.20-2.91 (m, 4H, CH$_2$CH$_2$); 1.60-1.59 (d, 3H, J=6.7 Hz, OCHCH$_3$); 1.25-1.20 (m, 3H, CH$_3$CH$_2$); 0.96-0.94 (m, 3H, J=7.0 Hz, CH$_3$CHNH). $^{13}$C NMRs (125 MHz CDCl$_3$, δ): 172.23, 161.34, 156.25, 129.69, 128.13, 127.60, 127.17, 126.10, 125.88, 115.22, 75.80, 72.62, 72.40, 61.23, 58.98, 49.72, 48.09, 34.28, 18.51, 14.08. MS-ESI m/z (%): 372 [M+H]$^+$(100). MS-MS (372): 354 (100), 221 (55), 147 (24), 121 (7).

Ethyl(R)-2-[4-[2-((1R,2S)-1-hydroxy-1-phenylpropan-2-yl-amino)ethyl]benzyl]propane (140 mg, 0.38 mM) is added to a solution of t-Boc$_2$O (156 mg, 0.71 mM) in THF (5 ml). The compound is maintained in agitation for 48 hours at room temperature and monitored by TLC (silica gel; mobile phase, ethyl acetate/petroleum ether=1:1), then it is concentrated at reduced pressure. The crude product is solubilized in ethyl acetate and washed with a solution of citric acid at 10%, a saturated aqueous solution of NaHCO$_3$ and subsequently with a saturated solution of NaCl. The organic phase is dried with Na$_2$SO$_4$, filtered and concentrated at reduced pressure. From the residue the product is isolated by column chromatography (silica gel; mobile phase: ethyl acetate/petroleum ether=1:9). 111 mg (yield of 66%) of N-tert-butyloxycarbonyl N—[(R)-ethyl 2-[4-[2-((1R,2 S)-1-hydroxy-1-phenyl-propan-2-yl-amino)ethyl]phenoxy]propane is obtained as a yellow oil. [α]D=+3.1 (c 0.66, CH Cl$_3$). FT-IR (neat): 3409, 2982, 2935, 1808, 1754, 1686, 1511, 1453, 1397, 1372, 1302, 1241, 1213, 1163, 1119, 1070, 845, 876 cm$^{-1}$. $^1$NMRs (400 MHz, CDCl$_3$, δ): 7.30-7.19 (m, 5H, aromatic protons); 7.01-6.99 (m, 2H, aromatic protons); 6.78-6.75 (m, 2H, aromatic protons); 5.15-5.14 (d, 1H, J=4.0 Hz, CHOH); 4.89 (bs, 1H, CHOH: it exchanges with D$_2$O); 4.68-4.62 (q, 1H, J=7.1 Hz, CH$_3$CHCO); 4.19-4.14 (m, 2H, CH$_2$CH$_3$); 3.60-2.59 (m, 5H, CH$_2$CH$_2$ and CH$_3$CHNH); 1.56-1.55 (d, 3H, J=6.8 Hz, OCHCH$_3$); 1.40 (s, 9H, t-Bu); 1.22-1.19 (m, 61:1, CH$_3$CH$_2$ and CH$_3$CHNH). $^{13}$C NMRs (100 MHz CDCl$_3$, δ): 172.50, 156.40, 142.8, 132.39, 130.03, 129.91, 128.32, 127.51, 126.36, 115.39, 80.34, 72.90, 61.46, 50.85, 35.38, 28.65, 18.78, 14.34, 12.05. MS-ESI m/z (%): 494 [M+Na]$^+$(100). MS-MS (494): 438 (17), 394 (100).

MSCl (0.8 ml, 0.6 mM) is added dropwise to a solution of N-tert-butyloxycarbonyl N—[(R)-ethyl 2-[4-[2-((1R,2 S)-1-hydroxy-1-phenylpropan-2-yl-amino)ethyl]phenoxy]propane (101 mg, 0.27 mM) and triethylamine (0.14 ml, 1.08 mM) maintained 5° C. The mixture is maintained at room temperature for 72 hours [TLC (silica gel; mobile phase: ethyl acetate/petroleum ether=3:7]. The reaction mixture is then washed with HCl (1M) and a saturated aqueous solution of NaHCO$_3$. The organic phase is dried with anhydrous Na$_2$SO$_4$, filtered and the solvent removed at reduced pressure. The product is isolated by column chromatography (silica gel; mobile phase: ethyl acetate/petroleum ether=3:7) from the crude reaction product giving 108 mg (quantitative yield) of (R)-ethyl 2-[4-[2-((4S,5S)-4-methyl-5-phenyloxazolidin-2-one)ethyl]phenoxy]propane as a yellow oil. [α]D=+16.1 (c 1.05, CH Cl$_3$). FT-1R (neat): 3063, 2985, 2930, 2253, 1751, 1612, 1512, 1458, 1417, 1377, 1266, 1238, 1200, 1135, 1017, 910, 826, 736 cm$^{-1}$. $^1$NMRs (400 MHz, CDCl$_3$, δ): 7.34-7.19 (m, 5H, aromatic protons); 7.06-7.04 (m, 2H, aromatic protons); 6.75-6.73 (m, 2H, aromatic protons); 4.82-4.80 (d, 1H, J=7.2 Hz, CHC6H5); 4.68-4.63 (q, 1H, J=6.8 Hz, CH$_3$CHCO); 4.20-4.14 (q, 2H, J=7.1 Hz CH$_2$CH$_3$); 3.67-3.60 (m, 1H, CH$_3$CHNH); 3.50-2.70 (m, 4H, CH$_2$CH$_2$); 1.57-1.56 (d, 3H, J=6.8 Hz, OCHCH$_3$); 1.22-1.19 (m, 6H, CH$_3$CH$_2$ and CH₃CHNH). ¹³C NMRs (100 MHz CDCl₃, δ): 172.43, 157.57, 156.56, 138.05, 131.44, 130.06, 129.10, 129.01, 126.09, 115.44, 82.63, 72.86, 61.47, 59.63, 43.33, 33.06, 18.76, 17.78, 14.35. MS-ESI m/z (%): 420 [M+Na]⁺(100). MS-MS (420): 420 (14), 392 (100), 376 (56), 320 (65), 213 (15), 141 (7).

Examples 12-22

Preparation of the Acids (Compounds of formula II, $R_5$=H)

NaOH 1N (8.4 ml, 8.4 mM) is added to a solution of 4.2 mole of one of the esters of Examples 1 to 10 in THF (10 ml). The mixture is now maintained in agitation for 1 at room temperature. The THF is removed under vacuum and HCl is added 2N up to pH=6. A precipitate is formed that is taken up and washed with water. The residue is treated with acetone to obtain the crystalline product.

The following compounds are thus obtained:

(±)-2-{4-[2-(2-phenyl-2-hydroxyethylamino)ethyl]phenoxy}-2-methylpropionic acid (1a)

Example 12

Pf 223° C. (dec), white solid (Yield=35%). FT-IR (KBr): 3650-3200, 3000, 2987, 2935, 2792, 1613, 1560, 1512, 1462, 1402, 1362, 1243, 1199, 1151, 837, 703 cm⁻¹. ¹NMRs (300 MHz DMSO-d₆δ): 1.38 (s, 6H, C(CH₃)₂), 2.57-2.82 (m, 6H, CH₂CHOH, CH₂NH, CH₂CH₂NH), 3.00-4.60 (bs, 3H, OH, NH and COOH: exchanged with D₂O), 4.72 (dd, J=5.8 and 2.6 Hz, 1H, CHOH), 6.69-6.72 (m, 2H, aromatic protons), 6.86-6.88 (m, 2H, aromatic protons), 7.19-7.34 (m, 5H, aromatic protons). MS-ESI m/z (%): 344 [M+H]⁺(100%). MS-ESI m/z (%): 342 [M−H]-(100%). Anal. (C₂₀H₂₅NO₄): C, H, N.

(2R)-(−)-2-{4-[2-(2-phenyl-2-hydroxyethylamino)ethyl]phenoxy}-2-methylpropionic acid (1b)

Example 13

Pf 232-233° C. (dec.), white solid (Yield=61%). [α]D=−21.3 (c=0.34, CH₃COOH). The analytical data are identical to those of (1a).

(2S)-(+)-2-{4-[2-(2-phenyl-2-hydroxyethylamino)ethyl]phenoxy}-2-methylpropionic acid (1c)

Example 14

Pf 232-233° C. (dec.), white solid (Yield=45%). [α]D=+23.6 (c=0.86, CH₃COOH). The analytical data are identical to those of (1a).

(±)-2-{4-[2-(2-phenyl-2-hydroxyethylamino)ethyl]phenoxy}propionic acid (1d)

Example 15

Pf 165-166° C., white solid (Yield=42%). FT-IR (KBr): 3600-3200, 2998, 2807, 1613, 1585, 1511, 1453, 1423, 1227, 1138, 1099, 1037, 932, 816, 747, 698 cm⁻¹. ¹NMRs (500 MHz acetic acid-d₄&): 1.61 (d, J=6.8 Hz, 3H, CHCH₃), 3.06-3.08 (m, 2H, CH₂CH₂NH), 3.27 (dd, J=12.5 and 10.7 Hz, 1H, CH₂CHOH), 3.31-3.37 (m, 2H, CH₂NH), 3.41 (dd, J=12.5 and 2.5 Hz, 1H, CH₂CHOH), 4.84 (q, J=6.8 Hz, 1H, CHCH₃), 5.26 (dd, J=10.7 and 2.5 Hz, 1H, CHOH), 6.86-6.88 (m, 2H, aromatic protons), 7.18-7.19 (m, 2H, aromatic protons), 7.28-7.31 (m, 1H, aromatic proton), 7.34-7.37 (m, 2H, aromatic protons), 7.39-7.41 (m, 2H, aromatic protons). ¹³C NMRs (75 MHz CDCl₃, δ): 17.84, 31.24, 49.56, 54.15, 69:45, 72.18, 115.50, 126.04, 128.43, 128.78, 129.76, 130.12, 140.26, 156.91, 176.99. MS-ESI m/z (%): 330 [M+H]⁺(100%). MS-ESI m/z (%): 328 [M−H]-(100%). Anal. (C₁₉H₂₃NO₄): C, H, N.

(2S)-(+)-2-{4-[2-((2S)-2-phenyl-2-hydroxyethylamino)ethyl]phenoxy}propionic acid (1e)

Example 16

Pf 202° C. (dec.), white solid (Yield=45%). [α]D=+0.68 (c=1.19, CH₃COOH). The analytical data are identical to those of (1d).

(2S)-(−)-2-{4-[2-((2R)-2-phenyl-2-hydroxyethylamino)ethyl]phenoxy}propionic acid (1f)

Example 17

Pf 193-194° C., white solid (Yield=41%). [α]D=−48.2 (c=1.04, CH₃COOH). The analytical data are identical to those of (1d).

(2R)-(+)-2-{4-[2-((2S)-2-phenyl-2-hydroxyethylamino)ethyl]phenoxy}propionic acid (1g)

Example 18

Pf 193-194.5° C., white solid (Yield=65%). [α]D=+44.89 (c=1.00, CH₃COOH). The analytical data are identical to those of (1d).

(2R)-(−)-2-{4-[2-((2R)-2-phenyl-2-hydroxyethylamino)ethyl]phenoxy}propionic acid (1h)

Example 19

Pf 202° C. (dec.), white solid (Yield=48%). [α]D=−0.41 (c=0.92, CH₃COOH). The analytical data are identical to those of (1d).

2-[4-[2-((R)-2-(3-chlorophenyl)-2-hydroxyethylamino)ethyl]phenoxy]-2-methyl propionic acid (1i)

Example 20

NaOH 1N (1 ml, 0.99 mM) is added to a solution of ethyl 2-[4-[2-((R)-2-(3-chlorophenyl)-2-hydroxyethylamino) ethyl]phenoxy]-2-methylpropane (200 mg, 0.49 mM) in THF (2 nil). The reaction is maintained at room temperature for 42 hours.

The solvent is then removed at reduced pressure and then 1M HCl is added dropwise up to pH=6. A precipitate is formed that is filtered and washed three times with water and ethanol. 90 mg of product is obtained (yield of 47%). Pf 218.5-220.3° C.s. FT-IR (neat): 3465, 2998, 2930, 2778, 2454, 1892, 1614, 1557, 1511, 1463, 1432, 1403, 1361, 1243, 1198, 1151, 1028, 836, 782, 693, 607 cm⁻¹; ¹H NMRs (400 MHz CD3COOD, δ): 7.42 (s, 1H, NH); 7.42-7.23 (m, 4H, aromatic protons); 7.16-7.14 (d, 2H, J=8.3 Hz, aromatic protons); 6.89-6.88 (d, 2H, J=8.3 Hz, aromatic protons); 5.20-

5.18 (m, 1H, CHOH); 3.44-3.24 (m, 4H, J=7.1 Hz, CH$_2$NH CH$_2$); 3.04-3.00 (m, 2H, CH$_2$C$_6$H$_4$); 2.36 (s, 6H, C(CH$_3$)$_2$). $^{13}$C NMRs (100 MHz CDCl$_3$, δ): 174.27, 153.91, 144.43, 134.30, 132.53, 129.67, 129.95, 127.62, 125.94, 123.92, 119.39, 79.05, 70.42, 61.38, 56.37, 50.38, 34.62, 25.31, 14.06. MS-ESI m/z (%): 378 [M+H]$^+$(100). MS-MS (378): 360 (100), 274 (41), 207 (57), 121 (76). Anal. Calc. for C$_{20}$H$_{23}$NO$_4$Cl: C, 63.79; H, 6.14; N, 3.71. Found: C, 64.06; H, 6.10; N, 3.98.

(R)-2-[4([2-((1S,2R)-1-hydroxy-1-phenylpropan-2-yl-amino)ethyl]phenoxy]propionic acid (1j)

Example 21

A solution of ethyl (R)-2-[4-[2-((1S,2R)-1-hydroxy-1-phenylpropan-2-yl-amino)ethyl]phenoxy]propane (210 mg, 0.6 mM) in NaOH 1N (1 mL) and THF (2 mL) is maintained in magnetic agitation for 5 hours at room temperature. Then, HCl 2N (2 mL) is added dropwise to the reaction mixture. The precipitate that is formed is filtered, crystallized from methanol and then recrystallized from hot acetone. A white solid is obtained (yield of 44%). Pf 140° C. (dec.). [α]D=+22.7 (c 0.50, MeOH). FT-IR (1(13r): 3417, 3301, 2923, 2852, 1735, 1614, 1555, 1513, 1456, 1384, 1241, 1136, 1084, 1049, 991, 827, 743, 704 cm$^{-1}$. $^1$NMRs (500 MHz, CD3COOD, δ): 10.76 (bs, 1H, COOH: exchanges with D$_2$O); 7.45-6.90 (m, 9H, aromatic protons); 5.21-5.20 (d, 1H, J=3.6 Hz, CHOH); 4.92-4.88 (m, 1H, CH$_3$CHCO); 3.56-3.54 (m, 1H, CH$_3$CHNH); 3.34-3.33 (m, 4H, NHCH$_2$ and OH); 3.07-3.03 (m, 2H, NHCH$_2$CH$_2$); 1.60-1.59 (d, 3H, J=6.5 Hz, CH$_3$CHCOOH); 1.11-1.09 (d, 3H, J=7.0 Hz, CH$_3$CHNH). $^{13}$C NMRs (125 MHz CDCl$_3$, δ): 176.33, 158.27, 141.64, 130.98, 130.92, 129.55, 128.92, 126.95, 116.61, 73.57, 71.59, 60.46, 52.77, 32.61, 18.84, 10.13. MS-ESI m/z (%): 342 [M+H]$^+$(100). MS-MS (342): 342 (7), 298 (4), 270 (100), 162 (2).

(R)-2-[4-[2-((1S,2S)-1-hydroxy-1-phenylpropan-2-yl-amino)ethyl]phenoxy]propionic acid (1k)

Example 22

A compound of ethyl (R)-2-[4-[2-((4S,5S)-4-methyl-5-phenylozazolidin-2-one)ethyl]phenoxy]propane (108 mg, 0.27 mM) and KOH (75 mg, 1.35 mmol) in water (1 ml) and dioxane (1 ml) is refluxed for 36 hours [TLC (eluent, ethyl acetato/petroleum ether=8/2)]. The mixture is concentrated at reduced pressure and the residue is taken up in water and then 2N HCl is added until a white precipitate is formed (37 mg, 30% of yield). Pf 145° C.s (dec). [α]D=+5.8 (c 0.92, CH Cl$_3$). FT-IR (KBr): 3057, 2981, 2928, 1745, 1511, 1451, 1422, 1236, 1130, 1098, 1015, 759, 701 cm$^{-1}$. $^1$NMRs (500 MHz, CDCl$_3$, δ): 10.70 (bs, 1H, COOH: exchanges with D$_2$O); 7.40-7.20 (m, 5H, aromatic protons); 7.11-7.09 (d, 2H, aromatic protons); 6.79-6.78 (d, 2H, aromatic protons); 4.95-4.93 (d, 1H, J=7.5 Hz, CHOH); 4.72-4.68 (q, 1H, J=6.6 Hz OCHCOOH); 3.70-3.64 (m, 3H, CH$_3$CHNH and OH); 3.55-2.75 (m, 4H, CH$_2$CH$_2$); 1.56-1.55 (d, 3H, J=6.6 Hz, CH$_3$CHCOO); 1.26-1.25 (d, 3H, J=6.0 Hz, CH$_3$CHNH). $^{13}$C NMRs (125 MHz CDCl$_3$, δ): 176.38, 159.71, 158.01, 139.50, 132.47, 131.01, 130.03, 129.94, 129.21, 127.18, 116.57, 116.35, 116.29, 73.81, 60.88, 84.04, 43.83, 33.53, 19.02, 17.70.

Compounds of Formula (II)

Example 23

Preparation of (S)-1-(hetero)aryloxy-2-hydroxy-3-[4-(4-methoxybenzenesulfonyl)piperazin-1-yl]propane General Process.

A solution of 1-(4-methoxybenzenesulfonyl)piperazine (717 mg, 2.8 mM) and (S)-(hetero)aryloxymethyloxirane (2 mM) (prepared using known process) in anhydrous methanol (20 ml) is refluxed in a nitrogen atmosphere up to completion. The solvent is then removed under vacuum. The crude product is dissolved in ethyl acetate and the organic phase is washed with water, dried on anhydrous Na$_2$SO$_4$, filtered and the solvent removed under vacuum.

Example 24

(S)-2-hydroxy-3-[4-(4-methoxyphenylsulfonyl)piperazin-1-yl]-1-phenoxy propane (2a)

The process followed is the same as described in Example 23.
Time of the reaction: 24 h. The product is isolated as a white solid in (yield of 50%) by column chromatography (silica gel, mobile phase: petroleum ether/ethyl acetate=6:4 and then 1:1) of the crude reaction product. Pf 136.0-138.0° C. (CH Cl$_3$/hexane). [α]D=−11.7 (c 0.98, CHCl$_3$). FT-IR (KBr): 3496, 3030, 2950, 2851, 2819, 1600, 1577, 1500, 1465, 1345, 1331, 1303, 1248, 1136, 1112, 1095, 1040, 1022, 998, 990, 950, 884, 847, 816, 806, 752, 733, 693 cm$^{-1}$. $^1$NMRs (300 MHz CDCl$_3$, δ): 7.72-7.67 (m, 2H, aromatic protons); 7.29-7.23 (m, 21-1, aromatic protons); 7.03-6.98 (m, 2H, aromatic protons); 6.97-6.92 (m, 1H, aromatic proton); 6.90-6.86 (m, 2H, aromatic protons), 4.08-4.02 (m, 1H, CHOH); 3.94-3.92 (m, 2H, C$_6$H$_{50}$CH$_2$); 3.88 (s, 3H, OCH$_3$); 3.20-2.90 (bs, 5H, OH exchange with D$_2$O, and 2 CH$_2$N of piperazine); 2.79-2.72 (m, 2H, CH$_2$N of piperazine); 2.63-2.53 (m, 4H, CH$_2$N of piperazine and CHOHCH$_2$N). $^{13}$C NMRs (75 MHz CDCl$_3$, δ): 163.41, 158.75, 130.15, 129.71, 127.19, 121.37, 114.74, 114.53, 77.46, 70.15, 66.03, 60.51, 55.87, 52.72, 46.21. MS-ESI m/z (%): 407 [M+H]$^+$(10); 429 [M+Na]$^+$(100). Anal. Calc. for C$_{20}$H$_{26}$N$_2$O$_5$S: C, 59.09; H, 6.45; N, 6.89. Found: C, 59.38; H, 6.33; N, 7.03.

Example 25

(S)-2-hydroxy-1-(4-hydroxyphenoxy)-3-[4-(4-methoxyphenylsulfonyl)piperazin-1-yl]propane (2b)

Pd/C at 10% (290 mg) is suspended in a solution of (S)-1-(4-benzyloxyphenoxy)-2-hydroxy-3-[4-(4-(4-methoxyphenylsulfonyl)piperazin-1-yl)propane (Example 26) (583 mg, 1.14 mM) in CH$_2$Cl$_2$ (10 ml) and maintained in agitation in H$_2$ atmosphere (1 atm) for 18 hours. The catalyst is then removed by filtering the reaction mixture on Celite, and the solvent is distilled under vacuum. The oily residue is crystalized (ethyl acetate/petroleum ether). A white solid is obtained (90% of yield). Pf 148.3-149.2° C.s. [α]D=−7.6 (c 1.07, CH Cl$_3$). FT-IR (KBr): 3466, 3050, 2969, 2941, 2921, 2896, 2864, 1593, 1576, 1511, 1468, 1458, 1445, 1348, 1328, 1306, 1254, 1234, 1200, 1177, 1165, 1136, 1101, 1051, 1017, 946, 833, 804, 737 cm$^{-1}$. $^1$NMRs .(500 MHz CD3OD, δ): 7.90-7.80 (bs, 1H, OH); 7.71-7.68 (m, 2H, aromatic protons); 7.13-7.10 (m, 2H, aromatic protons); 6.75-6.73 (m, 2H, aromatic protons); 6.68-6.66 (m, 2H, aromatic protons); 4.00-3.98 (m, 1H, CHOH), 3.88 (s, 3H, OCH$_3$), 3.86-3.83 (dd, 1H, J=9.7 and 4.4 Hz, CH$_2$OAr); 3.80-3.77 (dd, 1H, J=9.7 and 5.9 Hz, CH$_2$OAr); 3.70-3.50 (bs, 1H, OH); 2.98 (m, 4H, 2 CH$_2$N of piperazine); 2.60 (m, 4H, 2 CH$_2$ of piperazine); 2.55-2.52 (dd, 1H, J=13.0 and 4.8 Hz, CHOHCH$_2$N); 2.50-2.46 (dd, 1H, J=13.0 and 7.5 Hz, CHOHCH$_2$N). $^{13}$C NMRs (75 MHz CD3OD, δ): 163.72, 152.47, 150.31, 129.97, 126.98, 115.60, 115.55014.25, 71.35, 67.31, 60.45, 55.08, 52.81, 46.07. MS-ESI m/z (%): 445 [M+Na]$^+$(100). MS-MS (445): 445(100), 335 (69), 292 (54), 279 (13), 250 (8), 222 (32). Anal. Calc. for C$_{20}$H$_{26}$N$_2$O$_5$S: C, 56.86; H, 6.20; N, 6.63. Found: C, 57.03; H, 6.16; N, 6.66.

Example 26

(S)-1-(4-benzyloxyphenoxy)-2-hydroxy-3-[4-(4-methoxybenzenesulfonyl)piperazin-1-yl]propane (2c)

The process followed is the same as described in Example 23.

Time of the reaction: 40 h. The product is isolated as a white solid (yield of 64%) by column chromatography (silica gel; mobile phase: CH$_2$Cl$_2$/ethyl acetate/petroleum ether=2:5:3) of the crude reaction product. Pf 149.8-151.6° C. (methanol). [α]D=−7.9 (c 1.0 CH Cl$_3$). FT-IR (1(13r): 3506, 3051, 2986, 2979, 2906, 2853, 2746, 1597, 1574, 1506, 1456, 1413, 1383, 1349, 1328, 1309, 1230, 1155, 1104, 1059, 1028, 927, 877, 832, 804, 788, 736, 698 cm$^{-1}$. $^1$NMRs (300 MHz CDCl$_3$, δ): 2.51-2.63 (m, 4H, two CH$_2$ piperazine); 2.73-2.80 (m, 2H, CH$_2$N); 3.05 (m, 4H, two CH$_2$ piperazine); 3.87-3.89 (m, 5H, CH$_3$O and CH$_2$O); 4.02-4.04 (m, 1H, CHOH); 5.00 (s, 2H, CH$_2$C$_6$H$_5$); 6.79-6.84 (m, 2H, aromatic protons); 6.86-6.91 (m, 2H, aromatic protons); 6.99-7.03 (m, 2H, aromatic protons); 7.29-7.43 (m, 5H, aromatic protons); 7.67-7.72 (m, 2H, aromatic protons). $^{13}$C NMRs (75 MHz CDCl$_3$, δ): 46.19, 52.70, 55.88, 60.51, 66.02, 70.86, 114.55, 115.70, 116.03, 127.08, 127.71, 128.16, 128.80, 130.16, 137.39, 153.10, 153.49, 163.42. MS-ESI m/z (%): 535 [M Na]+(100%). MS-MS (238): 535 (7), 444 (100), 292 (17), 222 (8). Anal. Calc. for C$_{27}$H$_{32}$N$_2$O$_3$S: C, 63.26; H, 6.29; N, 5.46. Found: C, 63.24; H, 6.28; N, 5.41.

Example 27

(S)-2-hydroxy-3-[4-(4-methoxyphenylsulfonyl)piperazin-1-yl]-1-(3-nitrophenoxy)propane (2d)

The process followed is the same as described in Example 23.

Time of the reaction: 24 h. The product is isolated as an oil (yield of 87%) by column chromatography (silica gel, mobile phase: petroleum ether/ethyl acetate=2:8. [α]D=−11.0 (c 1.15, CH Cl$_3$). FT-IR (neat): 3499, 3092, 3058, 2923, 2849, 1617, 1596, 1580, 1528, 1498, 1457, 1349, 1325, 1303, 1255, 1182, 1162, 1093, 1064, 1028, 945, 836, 805, 737, 706 cm$^{-1}$. $^1$NMRs (300 MHz CDCl$_3$, δ): 7.84-7.80 (m, 1H, aromatic proton); 7.73-7.65 (m, 3H, aromatic protons); 7.44-7.39 (dd, 1H, J=8.2 and 8.0 Hz, aromatic proton); 7.26-7.20 (m, 1H, aromatic proton); 7.03-6.96 (m, 2H, aromatic protons), 4.15-3.94 (m, 3H, O$_2$NC$_6$H$_4$OCH$_2$ and CHOH); 3.88 (s, 3H, OCH$_3$); 3.15-2.75 (bs, 5H, 2 CH$_2$N of piperazines and OH: it exchanges with D$_2$O); 2.81-2.74 (m, 2H, CHOHCH$_2$N); 2.64-2.52 (m, 4H, 2 CH$_2$N of piperazine). $^{13}$C NMRs (75 MHz CDCl$_3$, δ): 163.44, 127.10, 159.34, 149.37, 130.24, 130.14, 121.93, 116.40, 114.55, 109.08, 70.87, 65.72, 60.15, 55.88, 52.67, 46.20. MS-ESI m/z (%): 474 [M+Na]$^+$(100). Anal. Calc. for C$_{20}$H$_{25}$N$_3$O$_7$S: C, 53.21; H, 5.54; N, 9.31. Found: C, 53.14; H, 5.51; N, 9.41.

Example 28

(S)-1-(3-aminophenoxy)-2-hydroxy-3-[4-(4-methoxyphenylsulfonyl)piperazin-1-yl]propane (2e)

Pd(OH)$_2$/C at 20% [1.54 g, 2.2 mM Pd(OH)$_2$] is suspended in a solution of (S)-2-hydroxy-3-[4-(4-methoxyphenylsulfonyl)piperazin-1-yl]-1-(3-nitrophenoxy)propane (3.30 g, 7.73 mM) (Example 27) in ethyl acetate (43 ml). The mixture is maintained in agitation in atmosphere of H$_2$ (10 atm) for 30 hours. The catalyst is then removed by filtering the reaction mixture on Celite, and the solvent is distilled under vacuum. A white solid is obtained (97% of yield). Pf 138.5-139.6° C.s. [α]D=−10.7 (c 1.06, CHCl$_3$). FT-IR (KW): 3456, 3371, 3100, 3063, 2945, 2916, 2853, 1597, 1576, 1497, 1456, 1343, 1328, 1302, 1263, 1195, 1161, 1096, 948, 839, 809, 773, 737, 694, 660 cm$^{-1}$. $^1$NMRs (300 MHz CDCl$_3$, δ): 7.71-7.67 (m, 2H, aromatic protons); 7.05-6.98 (m, 3H, aromatic protons); 6.30-6.29 (d, 1H, J=2.2 Hz, aromatic proton); 6.27-6.26 (m, 1H, aromatic proton); 6.23-6.22 (t, J=2.2 Hz, 1H, aromatic proton); 4.05-3.97 (m, 1H, CHOH); 3.89-3.88 (m, 5H, CH$_2$O and OCH$_3$), 3.70-3.10 (bs, 5H, NH$_2$); 3.10-2.85 (bs, 5H, 2 CH$_2$N of piperazine and OH); 2.79-2.69 (m, 2H, CH$_2$N of piperazine); 2.58-2.45 (m, 41-1, CH$_2$N of piperazine and CHOHCH$_2$N). $^{13}$C NMRs (75 MHz CD3OD, δ): 163.39, 159.95, 148.03, 130.35, 130.16, 127.15, 114.51, 108.55, 104.67, 101.90, 70.09, 66.07, 60.46, 55.87, 52.69, 46.28. MS-ESI m/z (%): 444 [M+Na]$^+$(100). Anal. Calc. for C$_{20}$H$_{27}$N$_3$O$_5$S: C, 56.99; H, 6.46; N, 9.97. Found: C, 56.91; H, 6.41; N, 9.69.

Example 29

Preparation of (S)-1-(3-substituted sulfonylaminophenoxy)-2-hydroxy-3-[4-(4-methoxyphenylsulfonyl)piperazin-1-yl]propane General Process.

Acetic anhydride (1.67 ml, 17.6 mM) is added to a solution of (S)-2-hydroxy-3-[4-(4-methoxyphenylsulfonyl)piperazin-1-yl]-1-(3-nitrophenoxy)propane (1.99 g, 4.4 mM) (Example 27) in CH$_2$Cl$_2$ (4 ml) and pyridine (2 ml). The mixture is maintained in agitation for 21 hours at room temperature. Then it is treated with 1N HCl, followed by a saturated aqueous NaHCO$_3$ solution. The two phases are separated and the organic phase dried over Na$_2$SO$_4$, filtered and the solvent removed under vacuum. An oil is obtained from which the product (S)-2-acetoxy-3,4-(4-methoxyphenylsulfonyl)piperazin-1-yl-1-(3-nitrophenoxy) propane is isolated (yield of 69%) by column chromatography (silica gel, mobile phase: petroleum ether/ethyl acetate=1:1). [α]D=−10.0 (c 1.04, CHCl$_3$). FT-IR (neat): 3092, 2930, 2850, 1740, 1597, 1576, 1531, 1499, 1458, 1373, 1350, 1329, 1307, 1259, 1234, 1164, 1095, 944, 805, 737 cm$^{-1}$. $^1$NMRs (400 MHz CDCl$_3$, δ): 7.82-7.79 (m, 1H, aromatic proton); 7.68-7.65 (m, 3H, aromatic protons); 7.42-7.38.(t, 1H, J=8.2 Hz, aromatic proton); 7.21-7.18 (dd, 1H, J=8.4 Hz, 2.6 and 0.9 Hz, aromatic proton); 7.00-6.97 (m, 2H, aromatic protons); 5.30-5.20 (m, 1H, CHOAc); 4.17-4.13 (dd, 1H, J=10.3 and 3.5 Hz, CH$_2$OAr), 4.12-4.08 (dd, 1H, J=10.3 and 6.4 Hz, CH$_2$OAr); 3.86 (s, 3H, OCH$_3$); 3.10-2.90 (m, 4H, 2 CH$_2$N of piperazine); 2.70-2.50 (m, 6H, 2 CH$_2$N of piperazine and CHOHCH$_2$N); 2.04 (s, 3H, CH$_3$CO). $^{13}$C NMRs (100 MHz CDCl$_3$, δ): 170.29, 163.03, 158.88, 149.03, 129.99, 129.81, 126.92, 121.81, 116.15, 114.21, 108.63, 94.40, 68.08, 57.36, 55.56, 52.74, 46.01; 21.04. MS-ESI m/z (%): 494 [M+H]$^+$(22); 516 [M+Na]$^+$ (100). MS-MS (516): 516 (3), 435 (22), 434 (100), 295 (10), 269 (26), 263 (13). Anal. Calc. for $C_{22}H_{27}N_3O_8S$: C, 53.55; H, 5.48; N, 8.52. Found: C, 53.51; H, 5.41; N, 8.69.

Pd/C at 10% (70 mg) is suspended in a solution of (S)-2-acetoxy-3-[4-(4-(4-methoxyphenylsulfonypiperazin-1-yl-1-(3-nitrophenoxy)propane (1.406 g, 2.86 mM) in ethyl acetate (12 ml). The mixture is maintained in agitation $H_2$ (10 atm) for 24 hours. Then, the catalyst is filtered on Celite and the solvent is distilled under vacuum. An oily product is obtained comprising (S)-2-acetoxy-1-(3-aminophenoxy)-3-[4-(4-methoxyphenylsulfonypiperazin-1-yl]propane at a yield of 99%. [α]D=−12.8 (c 1.06, $CHCl_3$). FT-IR (neat): 3460, 3381, 2928, 2851, 1737, 1597, 1497, 1458, 1374, 1347, 1331, 1303, 1261, 1240, 1191; 1164, 1095, 947, 836, 806, 736 cm$^{-1}$. $^1$NMRs (400 MHz $CDCl_3$, δ): 7.68-7.64 (m, 2H, aromatic protons); 7.08-6.96 (m, 3H, aromatic protons); 6.28-6.23 (m, 2H, aromatic protons); 6.19-6.18 (dd, 1H, J=2.4 and 2.2 Hz, aromatic proton); 5.23-5.18 (m, 1H, CHOAc), 4.35-3.50 (bs, 2H, $NH_2$); 4.00-3.97 (dd, 1H, J=10.5 and 4.1 Hz, $CH_2OAr$); 3.97-3.93 (dd, 1H, J=10.5 and 5.1 Hz, $CH_2OAr$); 3.86 (s, 3H, $OCH_3$); 3.06-2.90 (m, 4H, 2 $CH_2N$ of piperazine); 2.72-2.56 (m, 6H, 2 $CH_2N$ of piperazine and $CHOHCH_2N$); 2.02 (s, 3H, $CH_3CO$). $^{13}$C NMRs (100 MHz $CDCl_3$, δ): 170.51, 163.07, 159.56, 147.83, 130.08, 129.87, 126.96, 114.26, 108.32, 104.300, 101.69, 69.36, 67.23, 57.56, 55.63, 55.60, 55.56, 52.65, 45.88, 21.18. MS-ESI m/z (%): 464 [M+H]$^+$(17); 486 [M+Na]$^+$(100). MS-MS (486): 404 (40), 295 (6), 148 (100). Anal. Calc. for $C_{22}H_{29}N_3O_6S$: C, 57.02; H, 6.26; N, 9.07. Found: C, 56.99; H, 6.21; N, 9.09.

A suitable sulfonyl chloride is added (1.2 mM) to a solution of (S)-1-(3-aminophenoxy)-2-acetoxy-3-[4-(4-methoxyphenylsulfonyl)piperazin-1-yl)propane (1 mM) in $CH_2Cl_2$ (1.2 ml) and pyridine (0.5 ml). The mixture is shaken at room temperature up to the completion of the reaction. It is then diluted with $CH_2Cl_2$, and washed with saturated aqueous solution of $Na_2CO_3$ and then with water. The organic phase is dried with anhydrous $Na_2SO_4$, filtered and the solvent is distilled under vacuum. (S)-2-acetoxy-3-[4-(4-methoxyphenylsulfonyl)piperazin-1-yl]-1-(3-sulfonylaminophenoxy) propane is obtained.

KOH 2N (3 ml, 6 mM) is added to a solution of (S)-2-acetoxy-3-[4-(4-methoxyphenylsulfonyl)piperazin-1-yl]-1-(3-sulfonylaminophenoxy)propane (1 mM) in THF (10 ml). The mixture is maintained in vigorous agitation at room temperature up to the completion of the reaction. Water is added and then extracted with ethyl acetate. The organic phase is dried with $Na_2SO_4$, filtered and the solvent is distilled under vacuum. (S)-1-(3-alkyl or arylsulfonylaminophenoxy)-2-hydroxy-3-[4-(4-methoxyphenylsulfonyl)piperazin-1-yl]propane is thus obtained. The following compounds are similarly obtained.

Example 30

(S)-2-hydroxy-1-(3-methanesulfonylaminophenoxy)-3-[4-(4-ethoxyphenylsulfonyl)piperazin-1-yl)propane (2f)

Time of the reaction: 16 h. The product is isolated as a gray solid (yield of 86%) by column chromatography (silica gel, mobile phase: petroleum ether/ethyl acetate=3:7). Pf 109.0-110.0° C. (hexane). [α]D=−7.6 (c 0.30, CH $Cl_3$). FT-IR (KBr): 3455, 3267, 3014, 2929, 2851, 1597, 1578, 1498, 1458, 1399, 1328, 1261, 1181, 1162, 1149, 1095, 1025, 946, 838, 806, 737 cm$^{-1}$. $^1$NMRs (400 MHz $CDCl_3$, δ): 7.71-7.64 (m, 2H, aromatic protons); 7.24-7.20 (dd, 1H, J=8.2 and 7.9 Hz, aromatic proton); 7.03-7.00 (m, 2H, aromatic protons); 6.83-6.82 (dd, 1H, J=3.8 and 2.0 Hz, aromatic proton); 6.76-6.74 (dd, 1H, J=7.9 and 1.9 Hz, aromatic proton); 6.71-6.69 (dd, 1H, J=8.2 and 2.4 Hz, aromatic proton), 4.06-4.01 (m, 1H, CHOH); 3.97-3.86 (m, 5H, $OCH_3$ and $CH_2OAr$); 3.10-2.98 (s, bs and a m superimposed, 8H, $CH_3SO_3$, OH and 2 $CH_2N$ of piperazine); 2.78-2.73 (m, 2H, $NCH_2CHOH$); 2.61-2.50 (m, 6H, 3 $CH_2N$ of piperazine). $^{13}$C NMRs (100 MHz $CDCl_3$, δ): 163.14, 159.58, 137.91, 130.48, 129.90, 126.78, 114.27, 112.87, 111.10, 106.91, 70.05, 65.56, 59.94, 55.62, 52.35, 46.01, 39.26. MS-ESI m/z (%): 500 [M+H]$^+$(3), 522 [M+Na]$^+$(100). MS-MS (522): 522 (55), 443 (26), 335 (22), 313 (65), 292 (11), 273 (10), 272 (100), 266 (25), 222 (18). Anal. Calc. for $C_{21}H_{29}N_3O_7S_2$: C, 50.49; H, 5.85; N, 8.41. Found: C, 50.28; H, 5.75; N, 8.55.

Example 31

(S)-1-(3-Benzenesulfonylaminophenoxy)-2-hydroxy-3-[4-(4-methoxyphenyl sulfonyl)piperazin-1-yl)propane (2g)

Time of the reaction: 17 h. The product is isolated as a white solid (yield of 66%) by column chromatography (silica gel, mobile phase: petroleum ether/ethyl acetate=3:7). Pf 127.5-128.3° C. (hexane). [α]D=−6.4 (c 1.05 CH $Cl_3$). FT-IR (KBr): 3503, 3256, 3100, 3070, 2924, 2852, 1597, 1578, 1498, 1458, 1448, 1345, 1329, 1309, 1261, 1158, 1112, 1093, 1025, 946, 836, 806, 736, 689 cm$^{-1}$. $^1$NMRs (400 MHz CD $Cl_3$, δ): 7.77-7.75 (m, 2H, aromatic protons); 7.72-7.68 (m, 2H, aromatic protons); 7.54-7.49 (m, 1H, aromatic proton); 7.43-7.39 (m, 2H, aromatic protons); 7.05-7.09 (dd, 1H, J=8.2 and 8.1 Hz, aromatic proton); 7.03-6.99 (m, 2H, aromatic protons); 6.72-6.71 (t, 1H, J=2.2 Hz, aromatic proton); 6.62-6.58 (m, 2H, aromatic protons); 4.04-3.98 (m, 1H, CHOH); 3.89-3.81 (m, 5l-1, $OCH_3$ and $CH_2OAr$); 3.10-2.98 (m, 5H, 2 $CH_2N$ of piperazine and OH); 2.76-2.72 (m, 2H, $CHOHCH_2N$); 2.57-2.46 (m, 4H, 2 $CH_2N$ of piperazine). $^{13}$C NMRs (100 MHz $CDCl_3$, δ): 163.25, 159.05, 138.90, 137.64, 133.02, 130.08, 129.86, 129.01, 127.13, 126.72, 114.38, 113.82, 111.42, 107.69, 69.79, 65.29, 60.27, 55.62, 52.50, 45.37. MS-ESI m/z (%): 584 [M+Na]$^+$(100). MS-MS (584): 443 (15), 335 (20), 335 (20), 328 (31), 313 (51), 292 (9), 272 (100), 269 (8), 222 (30), 174 (5). Anal. Calc. for $C_{26}H_{31}N_3O_7S_2$: C, 55.60; H, 5.56; N, 7.48. Found: C, 55.64: H, 5.65: N, 7.34.

Example 32

(S)-2-hydroxy-3-(4-(4-methoxyphenylsulfonyl)piperazin-1-yl)-1-(3-thiophenesulfonylaminophenoxy) propane (2h)

Time of the reaction: 19 h. The product is isolated as a brown solid (70% of yield) by column chromatography (silica gel, mobile phase: petroleum ether/ethyl acetate=4:6). Pf 123.0-123.9° C. (dec). [α]D=−6.4 (c 0.98, CH $Cl_3$). FT-IR (103r): 3478, 3252, 3100, 2925, 2852, 1596, 1578, 1498, 1458, 1404, 1345, 1329, 1308, 1262, 1154, 1113, 1094, 1020, 946, 836, 806, 736 cm$^{-1}$. $^1$NMRs (400 MHz $CDCl_3$, δ): 7.71-7.68 (m, 2H, aromatic protons); 7.52-7.50 (dd, 1H, J=4.9 and 1.3 Hz, aromatic proton); 7.49-7.48 (dd, 1H, J=3.8 and 1.3 Hz, aromatic proton); 7.14-7.10 (dd, 1H, J=8.2 and 8.1 Hz, aromatic proton); 7.02-7.00 (m, 2H, aromatic protons); 6.99-6.97 (dd, 1H, J=4.9 and 3.8 Hz, aromatic proton);

6.77-6.75 (t, 1H, J=2.2 Hz, aromatic proton), 6.76-6.64 (m, 2H, aromatic protons); 4.09-4.03 (m, 1H, CHOH); 3.92-3.85 (m, 6H, OCH$_3$, CH$_2$OAr and OH); 3.16-2.98 (m, 4H, 2 CH$_2$N of piperazine); 2.80-2.77 (m, 2H, CHOHCH$_2$N); 2.63-2.53 (m, 4H, 2 CH$_2$N of piperazine). $^{13}$C NMRs (100 MHz CDCl$_3$, δ): 163.16, 159.18, 139.28, 137.47, 132.80, 132.38, 130.06, 129.89, 127.29, 126.69, 114.31, 113.84, 111.65, 107.72, 69.99, 65.56, 59.91, 55.63, 52.35, 45.87, MS-ESI m/z (%): 590 [M+Na]$^+$(100). MS-MS (590): 443 (16), 335 (30), 334 (43), 314 (9), 313 (90), 273 (10), 272 (100), 269 (12), 222 (23). Anal. Calc. for C$_{24}$H$_{29}$N$_3$O$_7$S$_3$: C, 50.78; H, 5.15; N, 7.40. Found: C, 50.72; H, 5.02; N, 7.22.

Example 33

(S)-2-hydroxy-1-(napht-1-yloxy)-3-[4-(4-methoxyphenylsulfonyl)piperazin-1-yl)propane (2i)

The process followed is the same as described in Example 23.

Time of the reaction: 42 h. The product is isolated as a white solid (yield of 91%) by column chromatography (silica gel, mobile phase: petroleum ether/ethyl acetate=2:8). Pf 67.1-68.0° C. [α]D=42.1 (c 1.00 CHCl$_3$). FT-IR (KBr): 3449, 3098, 3053, 2924, 2850, 2823, 1596, 1580, 1498, 1457, 1348, 1329, 1303, 1261, 1241, 1162, 1100, 1066, 1021, 947, 836, 805, 794, 773, 736 cm$^{-1}$. $^1$NMRs (400 MHz CDCl$_3$, δ): 8.22-8.20 (m, 1H, aromatic proton); 7.80-7.78 (m, 1H, aromatic proton); 7.71-7.67 (m, 2H, aromatic protons); 7.51-7.42 (m, 3H, aromatic protons); 7.36-7.32 (m, 1H, aromatic protons); 7.02-6.98 (m, 2H, aromatic protons); 6.79-6.77 (m, 1H, aromatic proton); 4.21-4.16 (m, 1H, CHOH); 4.14-4.06 (m, 2H, C$_{10}$H$_7$OCH$_2$); 3.86 (s, 3H, OCH$_3$); 3.10-2.82 (bs, 5H, OH: exchanges with D$_2$O, and 2 CH$_2$N of piperazine); 2.78-2.73 (m, 2H, CH$_2$N of piperazine); 2.69-2.62 (m, 2H, CHOHCH$_2$N); 2.60-2.55 (m, 2H, CH$_2$N of piperazine). $^{13}$C NMRs (100 MHz CDCl$_3$, δ): 167.90, 158.94, 139.19, 134.65, 132.27, 131.52, 131.24, 130.51, 130.21, 130.04, 126.51, 125.43, 109.62, 119.02, 75.00, 70.66, 65.20, 60.40, 57.21, 50.76. MS-ESI m/z (%): 457 [M+H]$^+$(80); 479 [M+Na]$^+$ (100). MS-MS (479): 313 (100), 269 (26), 0.183 (12). Anal. Calc. for C$_{24}$H$_{28}$N$_2$O$_5$S: C, 63.14; H, 6.18; N, 6.14. Found: C, 63.17; H, 6.20; N, 5.90.

Example 34

(S)-1-(Carbazol-4-yloxy)-2-hydroxy-3-[4-(4-methoxybenzenesulfonyl)piperazin-1-yl)propane (2j)

The process followed is the same as described in Example 23.

Time of the reaction: 24 h. Chromatography: silica gel, mobile phase: petroleum ether/ethyl acetate=1:1. white solid (CH Cl$_3$/ethyl ether). Yield=0.52%. FT-IR (KBr): 3404, 3057, 2926, 2840, 1596, 1508, 1497, 1456, 1347, 1331, 1305, 1262, 1161, 1097, 1024, 947, 836, 806, 786, 755, 735 cm$^{-1}$. $^1$NMRs (300 MHz CDCl$_3$, δ): 2.54-2.65 (m, 2H, CH$_2$N), 2.67-2.69 (m, 2H, CH$_2$ piperazine), 3.04 (m, 4H, two CH$_2$ piperazine), 3.87 (s, 3H, CH$_3$O), 4.16-4.26 (m, 2H, CH$_2$O), 6.60-6.63 (d, J=8.0 Hz, 1H, aromatic proton), 6.97-7.02 (m, 2H, aromatic protons), 7.02-7.05 (d, J=7.7 Hz, 1H, aromatic proton), 7.18-7.40 (m, 4H, aromatic protons), 7.67-7.72 (m, 2H, aromatic protons), 8.20-8.22 (m, 1 aromatic proton and NH, exchange with D$_2$O). $^{13}$C NMRs (75 MHz DMSO-d$_6$δ): 46.24, 52.71, 55.88, 60.80, 66.28, 70.28, 101.35, 104.25, 110.40, 112.87, 114.53, 119.86, 122.63, 123.02, 125.30, 126.85, 127.04, 130.17, 138.97, 141.16, 155.22, 163.40. MS-ESI m/z (%): 238 [M–H]-(100%). MS-MS (494): 297 (100), 253 (7), 241 (14), 196 (11), 181 (5), 156 (5).

Preparation of Intermediary for the Compounds of Formula (I)

Example 35

The compounds of formula (IV) are obtained by reduction with Et$_3$SiH of their precursors prepared by acylation according to the following Scheme 1,

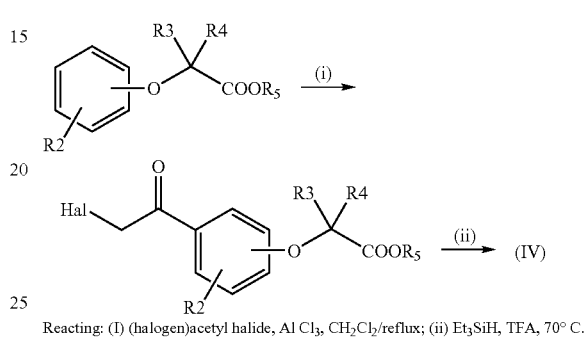

Reacting: (I) (halogen)acetyl halide, AlCl$_3$, CH$_2$Cl$_2$/reflux; (ii) Et$_3$SiH, TFA, 70° C.

Preparation of Intermediary for the Compounds of Formula (II)

Example 36

1-(4-methoxybenzenesulfonyl)piperazine synthesis

A solution of 4-methoxybenzenesulfonyl chloride (6.2 g, 30 mM) in CH$_2$Cl$_2$ (180 ml) is added to a solution of piperazine (12.9 g, 150 mM) in CH$_2$Cl$_2$ (570 ml) and pyridine (2.7 ml). The solution is maintained in agitation at room temperature for 15 h. The solvent is then removed under vacuum. The residue is dissolved in 3N HCl and washed with ethyl ether. The organic phase is removed and the aqueous phase is alkalized and extracted with ethyl acetate. The organic phase is dried over Na$_2$SO$_4$ and the solvent is removed under vacuum. A white solid is obtained (Yield=88%). P.f.: 184.3-185.6° C. FT-IR (KBr): 3082, 3058, 2975, 2944, 2907, 2840, 2810, 1597, 1580, 1495, 1465, 1442, 1413, 1346, 1318, 1298, 1286, 1254, 1179, 1159, 1110, 1095, 1066, 1027, 947, 830, 805, 734, 657, 634 cm$^{-1}$. $^1$NMRs (300 MHz CDCl$_3$, δ): 2.48-2.51 (m, 4H, two CH$_2$ piperazine), 2.88-2.94 (m, 5H, two CH$_2$ piperazine and NH), 3.86 (s, 3H, OCH$_3$), 6.95-7.00 (m, 2H, aromatic protons), 7.64-7.68 (m, 2H, aromatic protons). $^{13}$C NMRs (75 MHz CDCl$_3$, δ): 46.25, 50.57, 55.85, 77.82, 77.25, 77.67, 79.95, 114.40, 114.58, 127.32, 130.12, 163.27. GC-MS (70 eV) m/z (int. rel.): 258 [(34S)M+, 1], 256 [(32S)M+, 10], 171 (8), 108 (7), 92 (10), 85 (100), 77 (11), 64 (6), 63 (4), 56 (30). Anal. (C$_{11}$H$_{16}$N$_2$O$_3$S): Cal.: C, 51.54; H, 6.29; N, 10.93. Found: C, 51.59; H, 6.25; N, 10.96.

Example 37

Synthesis of (S)-(hetero)aryloxymethyloxirane

General Process

An appropriate phenol (7.7 mM) is added to a suspension of HNa (185 mg, 7.7 mM) in anhydrous N,N-dimethylformamide (40 ml), maintained at room temperature in agitation and in a nitrogen atmosphere. When the compound is clear, a solution of (S)-glycidyl m-nitrobenzenesulfonate (2 g, 7.7 mM) in anhydrous N,N-dimethylformamide (40 ml) is added dropwise. The mixture is left in agitation at room temperature until completion of the reaction. It is then diluted with water and extracted four times with ethyl acetate. The combined organic phases are washed three times with a saturated solution of $Na_2CO_3$, then with water, and dried over $Na_2SO_4$ and the solvent is removed under vacuum.

Example 38

(S)-(4-benzyloxyphenoxy)methyloxirane

Time of the reaction: 21 h. P.f.: 77.2-78.6° C. (ethyl acetate/hexane), white solid. Yield=65%. [α]D=+2.87 (c 1.01 CH $Cl_3$). FT-IR (KBr): 3104, 3062, 3035, 3010, 2908, 2876, 2861, 2918, 1510, 1452, 1466, 1386, 1337, 1288, 1239, 1225, 1136, 1120, 1041, 1030, 1018, 995, 918, 860, 826, 782, 733, 692 cm$^{-1}$. $^1$NMRs (300 MHz CD $Cl_3$, δ): 2.73-2.76 (dd, J=2.7 Hz and 4.9 Hz, 1H, $CH_2$ epoxide), 2.88-2.91 (dd, J=4.1 Hz and 4.9 Hz, 1H, $CH_2$ epoxide), 3.31-3.36 (m, 1H, CH epoxide), 3.89-3.94 (dd, J=5.5 Hz and 11.0 Hz, 1H, $CH_2O$), 4.15-4.19 (dd, J=3.3 Hz and 11.0 Hz, 1H, $CH_2O$), 5.02 (s, 2H, $CH_2C_6H_5$), 6.82-6.94 (m, 4H, aromatic protons), 7.29-7.44 (m, 5H, aromatic protons). $^{13}$C NMRs (75 MHz CDCl$_3$, δ): 44.97, 50.49, 69.70, 70.87, 115.91, 116.05, 127.72, 128.15, 128.79, 137.43, 153.08, 153.60. GC-MS (70 eV) m/z (int. rel.): 256 (M+, 22), 165 (4), 109 (2), 91 (100), 65 (8), 57 (7). Anal. ($C_{16}H_{16}O_3$): Cal.: C, 74.98; H, 6.29. Found: C, 74.80; H, 6.33.

Example 39

(S)-(Carbazol-4-yloxy)methyloxirane

Time of the reaction: 14 h. Solid brown. Chromatography: silica gel, mobile phase: petroleum ether/ethyl acetate=7:3. Yield=79%. [α]D=+17.2 (c 1.06 CH $Cl_3$). FT-IR (KBr): 3295, 3078, 3017, 2926, 1851, 1630, 1610, 1587, 1510, 1456, 1444, 1349, 1337, 1306, 1288, 1265, 1226, 1215, 1096, 1015, 904, 860, 796, 784, 755, 725 cm$^{-1}$. $^1$NMRs (300 MHz DMSO-d$_6$δ): 2.82-2.84 (add, J=2.5 Hz and 4.9 Hz, 1H, $CH_2$ epoxide), 2.90-2.93 (dd, J=4.4 Hz and 4.9 Hz, 1H, $CH_2$ epoxide), 3.50-3.55 (m, 1H, CH epoxide), 4.04-4.10 (dd, J=6.3 Hz and 11.3 Hz, 1H, $CH_2O$), 4.51-4.56 (dd, J=2.5 Hz and 11.3 Hz, 1H, $CH_2O$), 6.66-6.69 (d, J=8.0 Hz, 1H, aromatic proton), 7.07-7.10 (d, J=8.2 Hz, 1H, aromatic proton), 7.12-7.17 (t, J=7.4 Hz, 1H, aromatic proton), 7.25-7.36 (m, 2H, aromatic protons), 7.46-7.43 (d, J=8.0 Hz, 1H, aromatic proton), 8.15-8.17 (d, J=7.7 Hz, 1H, aromatic proton), 11.28 (br s, 1H, NH, exchange with $D_2O$). $^{13}$C NMRs (75 MHz DMSO-d$_6$δ): 44.50, 50.62, 69.44, 101.35, 104.93, 111.16, 112.16, 119.34, 122.25, 122.98, 12535, 127.14, 139.64, 141.81, 155.17. MS-ESI m/z (%): 238 [M–H]-(67%). MS-MS (238): 220 (12), 208 (17), 194 (48), 183 (9), 182 (100), 181 (5). Anal. ($C_{15}H_{13}NO_2$): Cal.: C, 75.30; H, 5.48; N, 5.85. Found: C, 75.28; H, 5.50; N, 5.86.

Example 40

(S)-2-acetoxy-1-(3-methanesulfonylaminophenoxy)-3-[4-(4-methoxyphenyl sulfonyl)piperazin-1-yl]propane The process followed is the same as described in Example 29.

Time of the reaction: 17 hours. The product is isolated as an oil (yield of 75%) by column chromatography (silica gel; mobile phase: petroleum ether/ethyl acetate=4:6) of the crude reaction product. [α]D=–8.3 (c 1.00 CH $Cl_3$). FT-IR (neat): 3453, 3263, 2929, 2851, 1739, 1597, 1499, 1458, 1329, 1261, 1238, 1163, 1149, 1095, 947, 806, 737 cm$^{-1}$. $^1$NMRs (400 MHz CDCl$_3$, δ): 7.68-7.64 (m, 2H, aromatic protons); 7.20-7.16 (t, 1H, J=8.1 Hz, aromatic proton); 7.12 (bs, 1H, NH); 7.00-6.96 (m, 2H, aromatic protons); 6.81-6.80 (t, 1H, J=2.2 Hz, aromatic proton); 6.78-6.76 (dd, 1H, J=7.9 and 1.5 Hz, aromatic proton); 6.66-6.64 (m, 1H, aromatic proton); 5.24-5.17 (m, 1H, CHOAc); 4.05-4.01 (dd, 1H, J=10.3 and 3.8 Hz, $CH_2OAr$); 4.01-3.97 (dd, 1H, J=10.3 and 5.1 Hz, $CH_2OAr$); 3.85 (s, 3H, $OCH_3$); 3.02-2.92 (m, 7H, $CH_3SO_3$ and 2 $CH_2N$ of piperazine); 2.65-2.55 (m, 6H, 2 $CH_2N$ of piperazine and CHOHCH$_2$N); 2.02 (s, 3H, $CH_3CO$). $^{13}$C NMRs (100 MHz CDCl$_3$, δ): 170.46. 163.02, 159.38, 138.10, 130.36, 129.86, 129.79, 126.91, 114.19, 112.97, 111.18, 106.91, 69.19, 67.55, 57.48, 55.62, 55.51, 52.64, 45.97, 39.11, 21.10.

Example 41

(S)-2-acetoxy-1-(3-benzenesulfonylaminophenoxy)-3-[4-(4-methoxyphenyl sulfonyl)piperazin-1-yl]propane The process followed is the same as described in Example 29.

Time of the reaction: 17 hours. The product is isolated as an oil (yield of 80%) by column chromatography (silica gel; mobile phase: petroleum ether/ethyl acetate=4:6). [α]D=–9.5 (c 0.99, CH $Cl_3$). FT-IR (neat): 3433, 3257, 3066, 2922, 2850, 1739, 1597, 1498, 1458, 1346, 1330, 1262, 1238, 1156, 1094, 947, 736 cm$^{-1}$. $^1$NMRs (400 MHz CDCl$_3$, δ): 7.78-7.76 (m, 2H, aromatic protons); 7.68-7.65 (m, 2H, aromatic protons); 7.53-7.50 (m, 1H, aromatic proton); 7.42-7.38 (dd, 2H, J=8.0 and 7.3 Hz, aromatic protons); 7.35-7.30 (bs, 1H, NH); 7.06-7.02 (t, 1H, J=8.2 Hz, aromatic proton); 7.00-6.96 (m, 2H, aromatic protons); 6.71-6.70 (t, 1H, J=2.2 Hz, aromatic proton), 6.61-6.56 (m, 2H, aromatic protons); 5.22-5.14 (m, 1H, CHOAc); 3.99-3.95 (dd, 1H, J=10.2 and 3.8 Hz, $CH_2OAr$); 3.95-3.91 (dd, 1H, J=10.2 and 5.3 Hz, $CH_2OAr$); 3.85 (s, 3H, $OCH_3$); 3.02-2.90 (m, 4H, 2 $CH_2N$ of piperazine); 2.70-2.50 (m, 6H, 2 $CH_2N$ of piperazine and CHOHCH$_2$N); 2.03 (s, 3H, $CH_3CO$). $^{13}$C NMRs (100 MHz CDCl$_3$, δ): 170.42, 163.03, 159.08, 138.92, 132.94, 129.85, 129.80, 137.72, 128.93, 127.09, 126.94, 114.21, 113.69, 111.41; 107.63, 67.50, 57.47, 55.61, 55.51, 52.64, 45.93, 21.09.

Example 42

(S)-2-acetoxy-3-[4-(4-methoxyphenylsulfonyl)piperazin-1-yl]-1-(3-thiophenesulfonylaminophenoxy)propane The process followed is the same as described in Example 29.

Time of the reaction: 17 hours. The product is isolated as an oil (yield of 83%) by column chromatography (silica gel; mobile phase: petroleum ether/ethyl acetate=4:6). [α]D=–8.5 (c 1.05, CH $Cl_3$). FT-IR (neat): 3249, 3103, 2921, 2851, 1738, 1596, 1498, 1457, 1374, 1345, 1307, 1262, 1163, 1094, 1018, 946, 837, 806, 736, 693 cm$^{-1}$. $^1$NMRs (400 MHz CDCl$_3$, δ): 7.71-7.65 (m, 2H, aromatic protons); 7.51-7.48 (m, 3H, aromatic protons); 7.39-7.33 (abs, 1H, NH); 7.11-7.07 (dd, 1H, J=8.2 and 8.1 Hz, aromatic proton); 7.00-6.96 (m, 3H, aromatic protons); 6.76-6.75 (t, 1H, J=2.1 Hz, aromatic proton); 6.61-6.64 (m, 1H, aromatic proton); 5.22-5.17 (m, 1H, CHOAc); 4.02-3.98 (dd, 1H, J=10.4 and 3.8 Hz, CH$_2$OAr); 3.98-3.94 (dd, 1H, J=10.4 and 5.3 Hz, CH$_2$OAr); 3.85 (s, 3H, OCH$_3$); 3.02-2.90 (m, 4H, 2 CH$_2$N of piperazine); 2.68-2.52 (m, 6H, 2 CH$_2$N of piperazine and CHOHCH$_2$N); 2.02 (s, $^{13}$C NMRs (100 MHz CDCl$_3$, δ): 170.48, 163.03, 159.11, 139.29, 137.49, 132.80, 132.40, 129.86, 129.80, 127.30, 126.92, 113.85, 114.22, 111.81, 107.75, 67.54, 57.46, 55.63, 55.53, 52.64, 45.94, 21.11.

Pharmacological Activity

Example 43

Determination of the Activity on the beta-3 Adrenergic Receptor

The determination of the beta-3 adrenergic activity of the compounds of general formula (I) was performed by measuring the levels of cAMP in cell lines of CHO-K1 that express the cloned human beta-3 adrenergic receptor. The accumulation of cAMP is directly correlated to the beta-3 adrenergic activity of the compound and is a predictive measure of the effectiveness of the ligand. The accumulation of cAMP produced by the compounds 1a-1h was determined using the Dissociation Enhanced Lanthanide Fluorescence Immunoassay (DELFIA®, ° Gabriel, D.; Vernier, M.; Pfeifer, M. J.; Dasen, B.; Tenaillon, L.; Bouhelal, R. *Assay and Drug Development Technologies* 2003, 1, 291-303), endowed with greater sensitivity and greater accuracy than [α-$^{32}$P] radioisotope methods (Hoffmann, C.; Leitz, M. R.; Obendorf-Maass, S.; Lohse, M. J.; Klotz, K.-N. *Naunyn-Schmiedeberg's Arch. Pharmacol.* 2004, 369, 151-159) or [$^3$H] (Nannies, K. M.; Briend-Sutren, M. M.; Emorine, L. J.; Delavier-Klutchko, C.; Marullo, S.; Strosberg, A. D. *Eur. J. Biochem.* 1991, 196, 357-361) of determining the levels of cAMP in cell lines.

TABLE 1

β3-Adrenergic Activity of the compounds 1a-k and 2a-2j.

| Compounds | EC$_{50}$ (nM[a] ± SEM[b]) (IA %)[c] |
|---|---|
| 1a | 4.9 ± 0.25 (68) |
| 1b | 3.9 ± 2.1 (72) |
| 1c | 3.4 ± 0.8 (76) |
| 1d | 3.8 ± 0.7 (65) |
| 1e | 192 ± 19 (−64) |
| 1f | 2.2 ± 0.7 (50) |
| 1g | 176 ± 20 (−73) |
| 1h | 107 ± 37 (35) |
| 1i | nd[d] |
| 1j | 211 ± 10 (39) |
| 1k | 1.97 ± 0.9 (53) |
| 2a | 5.0 ± 1.9 (58) |
| 2b | 1.97 ± 0.92 (67) |
| 2c | 8.3 ± 1.94 (48) |
| 2d | 4.1 ± 1.93 (84) |
| 2e | nd[d] |
| 2f | nd[d] |
| 2g | nd[d] |
| 2h | nd[d] |
| 2i | 5.24 ± 1.08 (43) |
| 2j | 3.8 ± 1.8 (38) |

[a]The value of EC$_{50}$ represents the concentration of ligand that produces 50% of the maximum accumulation of cAMP;
[b]SEM, standard error obtained from at least three experiments (n ≥ 3);
[c]the maximum concentration of cAMP induced by isoproterenol (10$^{-4}$ M) and the concentration of cAMP obtained in absence of agonists are defined as equal to 100% and 0% respectively, and the maximum response of each compound is expressed as Intrinsic Activity (IA);
[d]nd = not determined.

FIG. 1 shows the results of the DELFIA test for 1a-1h (the curves follow the vertical order of the compounds indicated on the right).

To verify the selectivity of the ligands (I) for the cloned human adrenergic β1- and β2 receptors, compounds 1a-1h were submitted to binding tests (Table 2). At the concentration of [$^3$H]-dihydroalprenolol used in the binding experiments (see biological methods section), the specific bonds represent approximately 76% and 85% of the total binding respectively. All the ligands have a low affinity for both the β1- and β2-adrenergic receptors (K$_i$>7000 nM and K$_i$>5000 nM respectively).

TABLE 2

Affinity of 1a-1k and 2a-2j for human β1- and β2-adrenergic receptor subtypes.

| | Binding K$_i$, nM[a] (% activation at 10 μM) | | | Binding K$_i$, nM[a] (% activation at 10 μM) | |
|---|---|---|---|---|---|
| | β1 | β2 | Compounds | β1 | β2 |
| 1a | >7000 (18) | >5000 (24) | 2a | >7000 (30) | >5000 (3) |
| 1b | >7000 (8) | >5000 (1) | 2b | >7000 (21) | >5000 (12) |
| 1c | >7000 (13) | >5000 (5) | 2c | >7000 (38) | >5000 (16) |
| 1d | >7000 (37) | >5000 (24) | 2d | >7000 (45) | >5000 (2) |
| 1e | >7000 (14) | >5000 (9) | 2e | >7000 (40) | >5000 (18) |
| 1f | >7000 (28) | >5000 (1) | 2f | nd[b] | nd[b] |
| 1g | >7000 (10) | >5000 (1) | 2g | nd[b] | nd[b] |
| 1h | >7000 (6) | >5000 (2) | 2h | nd[b] | nd[b] |
| 1i | nd[b] | nd[b] | 2i | >7000 (63) | >2000 (76) |
| 1j | >7000 (20) | >5000 (21) | 2j | >7000 (3) | 177 ± 3.3 (87) |
| 1k | >7000 (0) | >5000 (20) | | | |

[a]K$_i$ (nM) was obtained according to the equation of Cheng-Prusoff (Cheng, Y. C.; Prusoff, W. H. Biochem. Pharmacol. 1973, 22, 3099-3108);
[b]nd = not determined Biological Methods Cell Culture and Preparation of Membranes The cell lines of "Chinese hamster ovary" (CHO) that individually express the three subtypes of the human adrenergic receptor β1, β2 or β3 were grown at 37° C. in an atmosphere composed of 5% of CO$_2$ and 95% of air in a culture medium of Dulbecco's Modified Eagle Medium with a nutrient mixture of F1$_2$ (DMEM/F1$_2$) supplemented with 10% of bovine fetal Serum, 2 mM of L-glutamine, 100 units/ml of penicillin G and 100 μg/ml of streptococcus.

The preconfluence cells were washed with cold PBS, removed from the surface of the plate, collected in cold lysis buffer (10×10$^6$/ml; 5 mM Tris/HCl, 2 mM EDTA, pH 7.4 at 4° C.) and homogenized with a Brinkmann Polytron (5 for 3×10 secs). The cell membranes obtained were then homogenized for 10 mins at 4° C. at 1000g. The supernatant was centrifuged at 10000 g for 30 min. at 4° C. The resultant membrane pellet was resuspended in cold incubation buffer (50 mM Tris/HCl, 10 mM $MgCl_2$, pH 7.4 for the binding experiments on the β1-adrenergic receptors; 50 mM Tris/HCl, pH 7.4 for the binding experiments of on the β2-adrenergic receptors) and its protein content was then determined. The membrane suspension obtained was used immediately or stored at −80° C. until used in the binding experiments.

Binding Experiments of 1a-1h for the β1- and β2-Adrenergic Receptors:

The saturation experiments were conducted by incubating the cell membranes (50 μg of protein) in 500 μl of incubation buffer, containing increasing concentrations of [$^3$H]-dihydroalprenolol (0.1 nM, 0.5 nM, 1 nM, 3 nM, 5 nM, 10 nM). The β1-adrenergic receptors were incubated at 30° C. for 30 min. while the, incubation lasted 90 min. in the case of the β2-adrenergic receptor. The non-specific binding was determined by parallel incubation with Alprenolol 10 μM. The reactions were stopped by rapid filtering on Whatman GF/C glassfiber filter equilibrated for 60 minutes in 0.5% polyethyleneamine for the β1-adrenergic receptor or 0.3% polyethyleneamine in the case the β2-adrenergic receptor. The filters were then washed (3×1 ml) with cold incubation buffer. The residual radioactivity of the filters was measured using a Beckmann LS6500 Multi-purpose scintillator.

The competitive experiments were conducted by incubation of 50 μg of protein with increasing quantities of the compound under examination (from $10^{-9}$M to $10^{-4}$M) and 4 nM [$^3$H]-dihydroalprenolol for the β1-adrenergic receptor or 0.4 nM for the β2-adrenergic receptor, in a total volume of 500 μl of incubation buffer. The non-specific binding was determined in the presence of Alprenolol 10 μM. The reactions were then stopped and radioactivity was measured using a Beckmann LS6500 Multi-purpose scintillator.

The value of $K_D$ for the aprenolol in the CHO that express the receptor β1-adrenergico was 12.49 nM and the Bmax 2970 fmol/mg of protein, while in the CHO that express the receptor β2-adrenergico the value of $K_D$ for the alprenolol was 0.50 nM and the Bmax 540 fmol/mg of protein.

Determination of the β3-Adrenergic Activity by DELFIA cAMP-Eu Assay

The DELFIA test (Dissociation Enhanced Lanthanide Fluorine Immuno Assay) used for measuring the levels of cAMP was performed according to the protocol supplied by PerkinElmer Life Science. The optimization of the experimental conditions (quantity of cells, times of incubation) is reported below.

A plate of confluence cells was trypsinized and the cells were resuspended in the aforementioned culture medium, sown at a concentration of 50000 cells/200 μl per well in a 96-well plate and cultivated overnight in a $CO_2$ incubator. The culture medium was then aspirated from every well and substituted with 1000 of culture substrate without serum, preheated at 37° C. The plate was then put back into a $CO_2$ incubator for 30 mins at 37° C. 500 of IBMX (3-isobutyl-1-methylxanthine) 1 mM, an inhibitor of the phosphodiesterase was then added to all the wells. In some wells 50 μl of forskolin (compound used for the validation of the DELFIA) was added at different concentrations (100 nM, 500 nM, 1 μM, 10 μM, 50 μM) and in the other wells 50 μl of the compounds to be tested at the same concentrations as the forskolin; the plate was then again incubated for 30 min at 37° C. The cells, at this point, were lysed and incubated at room temperature for 5 min. The plate was used immediately for measuring the levels of cAMP or stored at 4° C. until the measurement was carried out. The fluorescence was determined using a multilabel time-resolved fluorimetry technique performed on a PerkinElmer 1420 Victor®. The excitation and emission wavelengths were 340 nm and 615 nm respectively.

The invention claimed is:
1. A compound selected from:
(2S)-2-[4-[2-((2S)-2-phenyl-2-hydroxyethylamino)ethyl]phenoxy]propionic acid (1e); and
(2R)-2-[4-[2-((2S)-2-phenyl-2-hydroxyethylamino)ethyl]phenoxy]propionic acid (1g);
or salts or its alkyl esters.

* * * * *